United States Patent
Kuzelka

(10) Patent No.: US 11,179,538 B2
(45) Date of Patent: Nov. 23, 2021

(54) SYSTEMS FOR ANESTHETIC AGENT VAPORIZATION

(71) Applicant: General Electric Company, Schenectady, NY (US)

(72) Inventor: Russell James Kuzelka, McFarland, WI (US)

(73) Assignee: General Electric Company, Schenectady, NY (US)

( * ) Notice: Subject to any disclaimer, the term of this patent is extended or adjusted under 35 U.S.C. 154(b) by 697 days.

(21) Appl. No.: 15/721,650

(22) Filed: Sep. 29, 2017

(65) Prior Publication Data

US 2019/0099581 A1    Apr. 4, 2019

(51) Int. Cl.
| | | |
|---|---|---|
| *A61M 16/18* | (2006.01) | |
| *B01F 3/04* | (2006.01) | |
| *B01F 3/02* | (2006.01) | |
| *A61M 11/04* | (2006.01) | |
| *B01F 5/04* | (2006.01) | |

(Continued)

(52) U.S. Cl.
CPC .......... *A61M 16/18* (2013.01); *A61M 11/042* (2014.02); *A61M 16/024* (2017.08); *B01F 3/022* (2013.01); *B01F 3/04* (2013.01); *B01F 5/0461* (2013.01); *B01F 5/0498* (2013.01); *A61M 15/00* (2013.01); *A61M 16/0093* (2014.02); *A61M 16/14* (2013.01); *A61M 16/202* (2014.02); *A61M 16/203* (2014.02); *A61M 16/208* (2013.01); *A61M 2016/0027* (2013.01); *A61M 2016/0033* (2013.01); *A61M 2016/103* (2013.01); *A61M 2016/1025* (2013.01); *A61M 2016/1035* (2013.01); *A61M 2205/3306* (2013.01); *A61M 2205/3331* (2013.01); *A61M 2205/3358* (2013.01); *A61M 2205/3368* (2013.01); *A61M 2205/3372* (2013.01); *A61M 2205/3375* (2013.01); *A61M 2205/3386* (2013.01); *A61M 2205/3569* (2013.01);

(Continued)

(58) Field of Classification Search
CPC ....... A61M 16/18; A61M 15/00; B01F 3/022; B01F 3/04
See application file for complete search history.

(56) References Cited

U.S. PATENT DOCUMENTS

| | | | | |
|---|---|---|---|---|
| 3,593,710 A | * | 7/1971 | Eichelman | A61M 16/18 128/200.11 |
| 3,794,027 A | * | 2/1974 | Johnson | A61M 16/104 128/204.13 |

(Continued)

OTHER PUBLICATIONS

"PARI's Hydrate Wins Prestigious R&D 100 Award," PR Newswire Website, Available Online at https://www.thefreelibrary.com/PARI%27s+Hydrate+Wins+Prestigious+R%26D+100+Award.-a0170212314, Oct. 24, 2007, 2 pages.

*Primary Examiner* — Joseph D. Boecker
*Assistant Examiner* — Jonathan S Paciorek
(74) *Attorney, Agent, or Firm* — McCoy Russell LLP

(57) ABSTRACT

Methods and systems are provided for delivering anesthetic agent to a patient. In one embodiment, a liquid anesthetic agent container includes a base region, an interior of the base region configured to hold liquid anesthetic agent, an adapter region, and a capillary force vaporizer (CFV) housed in the adapter region. The adapter region includes a coupling end configured to couple to a patient breathing circuit to supply anesthetic agent vaporized by the CFV to a patient.

20 Claims, 11 Drawing Sheets

(51) Int. Cl.
  *A61M 16/00* (2006.01)
  *A61M 15/00* (2006.01)
  *A61M 16/20* (2006.01)
  *A61M 16/10* (2006.01)
  *A61M 16/14* (2006.01)

(52) U.S. Cl.
  CPC . *A61M 2205/3592* (2013.01); *A61M 2205/50* (2013.01); *A61M 2205/6054* (2013.01)

(56) References Cited

U.S. PATENT DOCUMENTS

| | | | | |
|---|---|---|---|---|
| 4,067,935 | A * | 1/1978 | Jones | A61M 16/18 128/203.14 |
| 4,406,302 | A * | 9/1983 | Olesen | A61M 16/209 137/514.5 |
| 4,693,853 | A * | 9/1987 | Falb | A61M 16/186 128/202.27 |
| 4,770,168 | A * | 9/1988 | Rusz | A61M 16/18 128/203.12 |
| 5,509,405 | A * | 4/1996 | Mashak | A61M 16/18 128/200.14 |
| 6,024,087 | A * | 2/2000 | Kersey | A61M 16/204 128/203.12 |
| 6,162,046 | A | 12/2000 | Young et al. | |
| 6,169,852 | B1 * | 1/2001 | Liao | F22B 1/284 261/142 |
| 6,308,572 | B1 * | 10/2001 | Ishikawa | G01N 29/024 73/24.01 |
| 6,347,936 | B1 | 2/2002 | Young et al. | |
| 6,634,864 | B1 | 10/2003 | Young et al. | |
| 7,431,570 | B2 | 10/2008 | Young et al. | |
| 7,788,901 | B2 * | 9/2010 | Huang | F02D 41/027 60/274 |
| 2006/0196968 | A1 * | 9/2006 | Rabin | A61M 11/042 239/136 |
| 2007/0137646 | A1 * | 6/2007 | Weinstein | A62B 9/003 128/204.17 |
| 2009/0220222 | A1 * | 9/2009 | Rabin | A01M 1/2077 392/396 |
| 2011/0045166 | A1 | 2/2011 | Shimmura | |
| 2011/0210458 | A1 | 9/2011 | Brodbeck et al. | |
| 2014/0053831 | A1 * | 2/2014 | Leamon | A61M 15/009 128/200.23 |
| 2016/0175555 | A1 * | 6/2016 | Heidschmidt | A61M 16/1075 128/203.14 |

\* cited by examiner

SYSTEMS FOR ANESTHETIC AGENT VAPORIZATION

FIELD

Embodiments of the subject matter disclosed herein relate to delivery of anesthetic agent, and more particularly, to vaporization of anesthetic agent using a capillary force vaporizer.

BACKGROUND

In order to perform surgery on a patient, an inhaled anesthetic agent may be supplied to the patient to provide temporary anesthesia to enable surgery and eliminate patient discomfort. The concentration of the anesthetic agent may be controlled to ensure sufficient anesthetic agent is provided for patient comfort without compromising patient safety. During general anesthesia, the central nervous system activity is suppressed, which results in unconsciousness and total lack of sensation. During sedative procedures, the central nervous system is suppressed to a lesser degree than general anesthesia; inhibiting both anxiety and creation of long-term memories without resulting in a total loss of consciousness. A traditional method for supplying anesthetic agent has been to absorb the liquid agent into a wick material and pass fresh incoming patient ventilation gas over the wick to evaporate the agent, with the concentration of agent vapor controlled by the amount of fresh gas flowing past the wick.

BRIEF DESCRIPTION

In one embodiment, a liquid anesthetic agent container includes a base region, an interior of the base region configured to hold liquid anesthetic agent, an adapter region, and a capillary force vaporizer (CFV) housed in the adapter region. The adapter region includes a coupling end configured to couple to a patient breathing circuit to supply anesthetic agent vaporized by the CFV to a patient. In this way, a low cost, light weight, and compact vaporizer in the form of a CFV may be integrated within the liquid anesthetic agent container, to form a self-contained vaporizer unit/anesthetic agent reservoir. In doing so, exposure hazards associated with filling vaporizers may be reduced, along with potential contamination associated with filling vaporizers.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

As explained above, tradition bypass anesthetic vaporizers use a large (heavy) thermal mass (e.g., brass) and a passive, saturated cotton wick to generate vapor for inhalation anesthesia. A traditional bypass vaporizer functions whereby a proportion of fresh gas flow (FGF) from the anesthesia machine is split into both a carrier gas and bypass gas. More than 80% of the flow (termed the bypass gas) passes straight through the bypass chamber to the vaporizer outlet with typically much less than 20% of the flow from the FGF being diverted through the vaporizing chamber (termed the carrier gas). Depending on the temperature and vapor pressure of the inhaled anesthetic, the flow through the vaporizing chamber entrains a specific flow of inhaled anesthetic. The flows through the bypass chamber and vaporizing chamber are rejoined at the outlet of the vaporizer. The final concentration of inhaled anesthetic is the ratio of the flow of the inhaled anesthetic to the total gas flow. Such a configuration is typically large, heavy, costly, and may not provide sufficient control over the amount of anesthetic delivered to the patient; especially at high fresh gas flow rates Thus, according to embodiments disclosed herein, an active capillary force vaporizer (CFV) may be used to provide an active, low cost, and compact mechanism to directly vaporize a liquid anesthetic or other vaporizable medication directly from a liquid reservoir/supply, thus reducing cost, size, weight (thermal mass), and enabling open or closed loop electronic control schemes. The anesthetic vaporized by the CFV may be drawn from an anesthetic liquid reservoir or directly from an anesthetic drug bottle, whereby the CFV unit is integrated into the bottle or a bottle adapter.

A programmable system including a CFV that generates pressurized vapor emissions may be used for generating and regulating anesthetic agent vapor emissions, both simplistically and economically. The CFV technology uses engineered ceramic materials to turn liquid into vapor instantly, efficiently, and without having any boiling liquid in a reservoir. The CFV is a thick film, high surface area boiler that combines capillary force and phase transition. By inducing phase transition in a capillary environment, the CFV imparts pressure onto the expanding gas and ejects it with significant force. Thus, a simple, low cost vaporizer is provided which enables control over a vapor output concentration that is proportional to the amount of electrical power delivered to the capillary force vaporizer.

Figure 11:
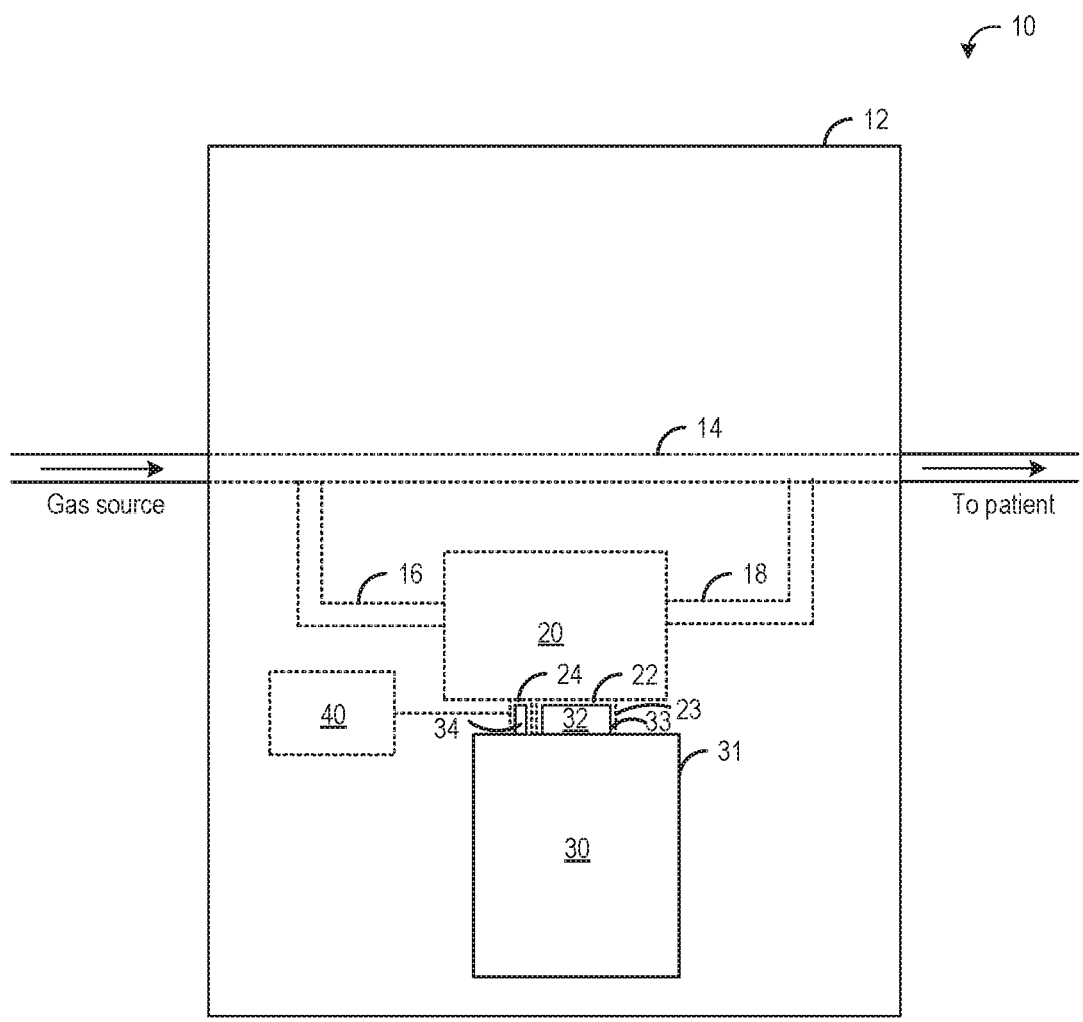
FIG. 11 schematically shows a patient gas machine.

FIG. 11 schematically shows a patient gas delivery system 10 in the form of an anesthesia machine 12. Anesthesia machine may include a gas passage 14. Gas passage 14 may receive fresh gas from a gas source. Fresh gas in the anesthesia machine may split into bypass gas and carrier gas, where the bypass gas flows along gas passage 14 to an outlet of the anesthesia machine. The carrier gas flows into inflow passage 16 and outflow passage 18, where it rejoins with the bypass gas, where the bypass gas and carrier gas are ultimately supplied to a patient (e.g., via a ventilator mechanism not shown in FIG. 11). The carrier gas may pick up vaporized anesthetic agent in a vapor reservoir 20. Vapor reservoir 20 may be configured to house vaporized anesthetic agent received via a port 22 of the vapor reservoir. Port 22 may couple to a liquid anesthetic agent container 30 (or reservoir) via a coupling end 32 of container 30. Container 30 may include a vaporizer to vaporize liquid anesthetic agent stored in container 30. The vaporizer may be supplied power from anesthesia machine via an electrical connection between a first electrical connector 24 of the anesthesia machine and a second electrical connector 34 of container 30. The power supply to the vaporizer may be modulated via a controller 40 of the anesthesia machine.

Figure 1:
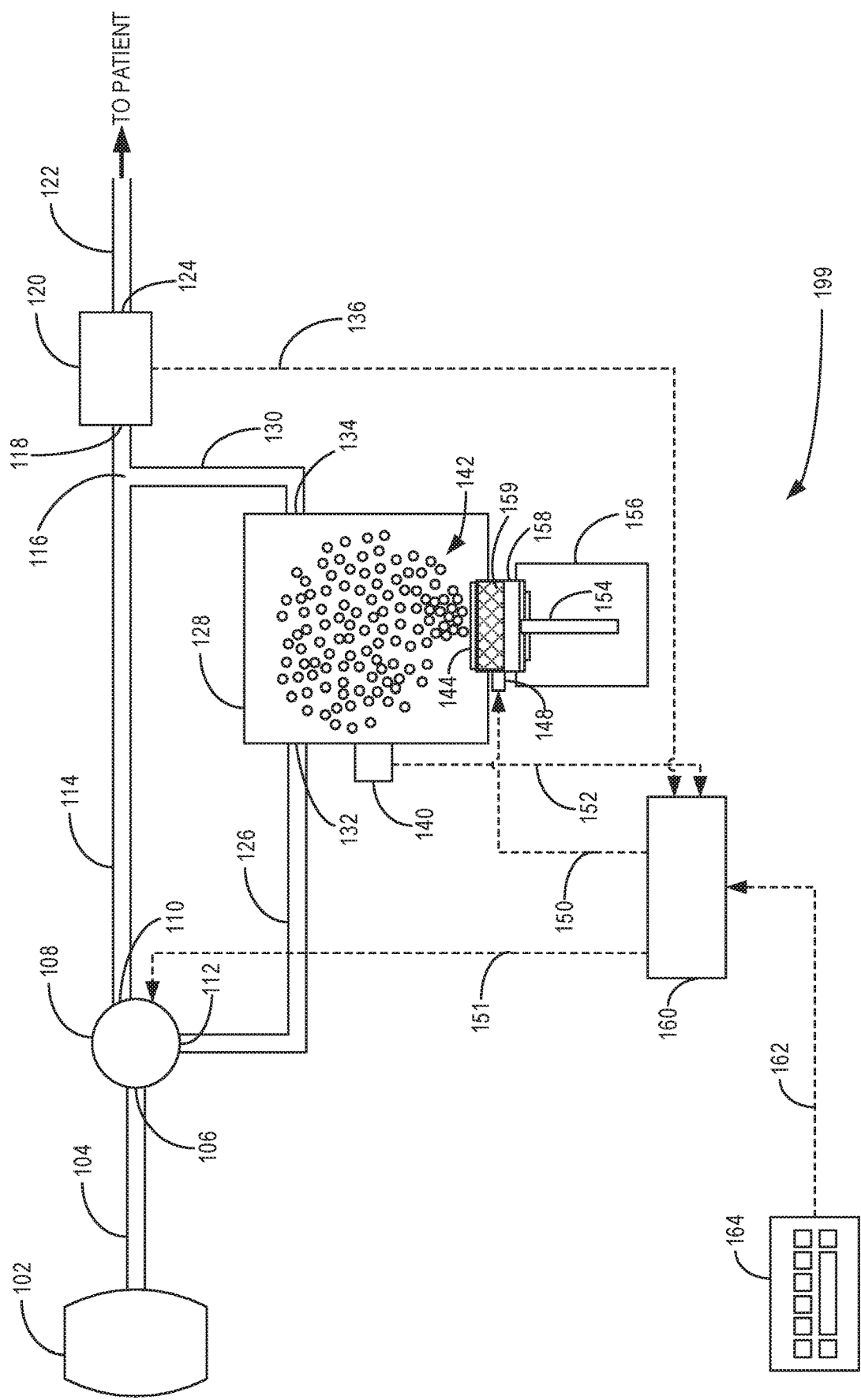
FIG. 1 schematically shows a first embodiment of an anesthetic agent delivery system.

Referring now to FIG. 1, a schematic view of an anesthetic delivery system 199 according to a first embodiment of the present disclosure is shown. The system 199 may be used in surgery and other medical procedures to maintain a partially closed breathing environment for the patient, through which a controlled and medically appropriate amount of anesthetic agent, in the form of a gas, may be administered.

System 199 includes a capillary force vaporizer (CFV) 158 fluidically coupled to an anesthetic agent reservoir 156 configured to store a suitable liquid anesthetic agent. Reservoir 156 may be a refillable reservoir that is not pressurized by an external pressure supply and is maintained at ambient temperature, for example. Upon activation of CFV 158, liquid anesthetic in reservoir 156 is drawn into CFV 158, where the anesthetic agent is vaporized and expelled to vapor reservoir 128.

CFV 158 includes a liquid supply 154 and a vaporizer 159. Liquid supply 154 may include a porous wick comprised of alumina ceramic in one example. The wick may extend into reservoir 156 and draw liquid anesthetic agent into CFV 158 via capillary action. Vaporizer 159 of CFV 158 may include a resistive heating element or other suitable heating element that is configured to vaporize the liquid drawn into CFV 158. The heater is configured such that heat travels opposite the liquid flow, from the vaporization zone toward the liquid intake region, as a cooling flow of fresh liquid travels toward the vapor release area, resulting in a dynamic balance of heat flux, liquid flow, and evolved vapor. A thermal insulating region may be present between liquid supply 154 and vaporizer 159 to prevent liquid supply 154 from being heated above the vaporization temperature of the liquid in reservoir 156. Vapor is released from CFV 158 via outlet 144 as a controllable (programmable) vapor flow 142.

The vapor flow 142 in vapor reservoir 128 mixes with fresh gas (also referred to as medical gas) and is supplied to a patient. The fresh gas is provided from a gas source 102, which may include pipes, tanks, or other suitable sources. The fresh gas may include fresh air, oxygen, nitrous oxide, and/or other suitable gas. The fresh gas is supplied from gas source 102 to a multi-outlet valve 108 via a first gas passage 104. The fresh gas enters multi-outlet valve 108 at a valve inlet 106 and is split into bypass gas and carrier gas. The bypass gas exits multi-outlet valve 108 via first valve outlet 110 to second gas passage 114. The carrier gas exits multi-outlet valve 108 via second valve outlet 112 and travels through third gas passage 126.

The carrier gas enters vapor reservoir 128 via vapor reservoir inlet 132 and mixes with the vaporized anesthetic. A mix of the carrier gas and vaporized anesthetic exits vapor reservoir via vapor reservoir outlet 134 and travels through fourth gas passage 130. At junction 116, second gas passage 114 and fourth gas passage 130 merge to form fifth gas passage 122. Thus, in fifth gas passage 122, the bypass gas mixes with the carrier gas and vaporized anesthetic to form a fresh gas/vaporized anesthetic mix, which is ultimately delivered to a patient. While not shown in FIG. 1, it is to be understood that fifth gas passage 122 may be coupled to a suitable patient delivery mechanism, such as a manual or mechanical ventilator, mouthpiece, or endotracheal tube.

A concentration sensor 120 is positioned in fifth gas passage 122. Concentration sensor 120 includes a concentration sensor inlet 118 and a concentration sensor outlet 124 through which the fresh gas/vaporized anesthetic mix flows. Concentration sensor 120 may be a suitable sensor that is configured to measure the concentration of one or more anesthetic agents in the fresh gas/vaporized anesthetic agent mix. In one example, the concentration sensor may be an optical sensor that emits suitable light (e.g., infrared) through the fresh gas/vaporized anesthetic agent mix and determines a concentration of the anesthetic agent based on absorption of the light. In other examples, the concentration sensor may be a carbon dioxide or oxygen sensor that measures the concentration of the anesthetic agent based on a displacement of the carbon dioxide or oxygen relative to the supplied concentration of carbon dioxide or oxygen in the fresh gas (e.g., upstream of where the vapor flow mixes with the carrier gas).

System 199 further includes a controller 160. Controller 160 includes a processor operatively connected to a memory. The memory may be a non-transitory computer-readable medium and may be configured to store computer executable code (e.g., instructions) to be processed by the processor in order to execute one or more routines as described herein. The memory may also be configured to store data received by the processor.

Controller 160 is configured to receive and process data. Data may be input by a user via a user input device 164 that is operationally connected to the processor and thus is configured to an input signal 162 to controller 160. User input device 164 may include a mouse, a keyboard, a voice input device, a touch input device for receiving a gesture from a user, a motion input device for detecting non-touch gestures and other motions by a user, and other comparable input devices and associated processing elements capable of receiving user input from a user, or a combination thereof. Controller 160 may be operatively connected to other computing devices, such as hospital computing devices (e.g., electronic medical record-storing devices, operating room workstations, and/or anesthesia delivery machines).

Controller 160 is configured to receive output from a plurality of sensors of system 199. As shown, controller 160 is operably coupled to concentration sensor 120, which sends a concentration signal 136 indicative of a concentration of anesthetic agent in the fresh gas/vaporized anesthetic mix to controller 160. Controller 160 is operably coupled to a reservoir pressure sensor 140, which sends a pressure signal 152 indicative of a pressure of vapor reservoir 128 to controller 160.

Controller 160 is configured to process the output received by the input device and sensors and adjust one or more actuators of system 199 in response to the received output. The one or more actuators that may be adjusted by controller 160 include a driver 148 of the heating element of CFV 158 (e.g., the resistive heating element of vaporizer 159) and multi-outlet valve 108. For example, controller 160 may send a heater control signal 150 to driver 148 to adjust the current or voltage supplied to the heating element of CFV 158. Controller 160 may send a valve control signal 151 to multi-outlet valve 108 to adjust the position of multi-outlet valve 108 in order to adjust the proportion of fresh gas that is supplied to vapor reservoir 128.

In this way, a concentration of anesthetic agent in the fresh gas/vaporized anesthetic mix supplied to the patient may be measured from output from concentration sensor 120. The concentration may be used by controller 160 to adjust an amount of current or voltage supplied to the heating element/vaporizer 159 of CFV 158, which results in a change of temperature of vaporizer 159 and hence a change in the amount of liquid agent that is vaporized and supplied to the patient. For example, controller 160 may modulate the electrical power applied to the CFV heating element based on an error signal obtained between the measured and a set anesthetic agent concentration (e.g., user set). Further, controller 160 may use the output of concentration sensor 120 to adjust a position of multi-outlet valve 108 in order to adjust a ratio of carrier gas to bypass gas.

By doing so, the CFV may be utilized as an "active wick" for traditional bypass vaporization, reducing size, weight, cost, and response time to changes in the fresh gas flow rate. Depending on the amount of heat energy provided to the heating element, a programmed amount of vapor will be evolved. Because of the thin-film nature of the liquid/vaporization layer interface, the CFV may have a very quick response time to step-change FGF flows and/or concentration commands. Because the CFV relies on capillary action, it can be used in any orientation so long as a liquid feed is provided to the structure; e.g., through another capillary wick, metering pump, or other such reservoir to communicate the fluid to be vaporized to the base porous layer of the CFV. Additionally, the CFV may provide a pressurized vapor flow that can be supplied to a patient without the use of moving parts (e.g., without injector valves), thus lowering costs and reducing maintenance issues associated with moving parts.

Certain characteristics of the CFV, such as material selection, pore size, pore size distribution, degree of porosity, thermal mass, and thermal conductivity, contribute to tradeoffs between liquid permeability and capillary pressure. For example, materials having higher liquid permeability generally provide higher volume throughput and materials with higher capillary pressure provide higher pressure vapor output. These characteristics may therefore be selected for a specific application, such as different materials or pore sizes for different anesthetic agents.

While FIG. 1 illustrates only a single CFV, the system of FIG. 1 may include more than one CFV. For example, two or three CFVs may be present (or a single, larger CFV element), each coupled to the same anesthetic agent reservoir and the same vapor reservoir. In this way, a desired amount of vaporized anesthetic agent may be generated. In some examples, various components of system 199 may be housed in a patient breathing machine, such as anesthesia machine 12 of FIG. 11. For example, vapor reservoir 128 and associated gas passages (e.g., passages 104, 114, 126, 130, and 122), controller 160, and sensor 120 may be housed in the patient breathing machine. CFV 158 and liquid anesthetic agent reservoir 156 may be a separate unit, similar to container 30 of FIG. 11, which couples to the patient breathing machine.

Figure 2:
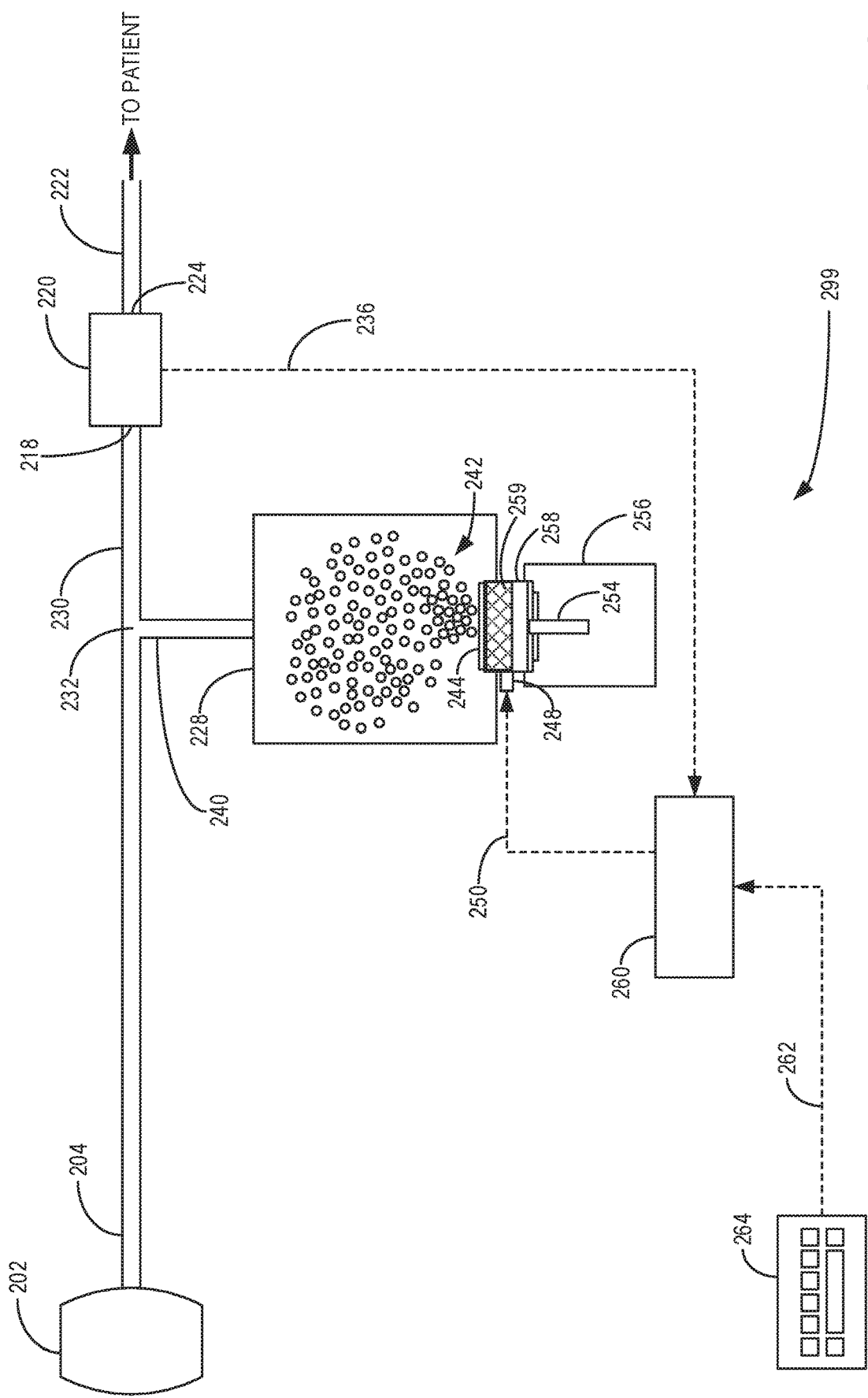
FIG. 2 schematically shows a second embodiment of an anesthetic agent delivery system.

FIG. 2 is a schematic view of an anesthetic delivery system 299 according to a second embodiment of the present disclosure. System 299 may be similar to system 199 of FIG. 1, but may be a direct vapor injection configuration rather the bypass configuration illustrated in FIG. 1. System 299 includes CFV 258 fluidically coupled to an anesthetic agent reservoir 256 configured to store a suitable liquid anesthetic agent. Reservoir 256 may be a refillable reservoir that is not pressurized by an external pressure supply and is maintained at ambient temperature, for example. Upon activation, liquid anesthetic agent in reservoir 256 is drawn into CFV 258, where the anesthetic is vaporized and expelled to vapor reservoir 228.

CFV 258 includes a liquid supply 254 and a vaporizer 259, similar to CFV 158 of FIG. 1 and hence description of CFV 158 likewise applies to CFV 258, where liquid supply 254 is configured to draw in liquid anesthetic agent and supply the liquid to vaporizer 259. A heating element of vaporizer 259 vaporizes the anesthetic agent, and an amount of liquid anesthetic agent vaporized may be proportional to a temperature of vaporizer 259. Vapor is released from CFV 258 via outlet 244 as a controllable (programmable) vapor flow 242.

System 299 includes a gas source 202 to supply fresh gas (also referred to as medical gas). Gas source 202 may include pipes, tanks, or other suitable sources. The fresh gas may include fresh air, oxygen, nitrous oxide, and/or other suitable gas. The fresh gas is supplied from gas source 202 to a junction 232 via a first passage 204.

At junction 232, vapor flow 242 from vapor reservoir 228 is injected via injector 240. Because the CFV generates a flow of pressurized vapor, injector 240 may be simply a pathway for the vapor flow to travel to junction 232. However, in other examples, injector 240 may include a valve or other structure to regulate the supply of vapor to junction 232. The injected vapor mixes with fresh gas from first gas passage 204 to form a fresh gas/vaporized anesthetic mix and the mix flows to a second gas passage 230 and is ultimately delivered to a patient via a third gas passage 222. In some examples, a venturi or other mixing device may be present to facilitate mixing of the vaporized anesthetic agent and fresh gas. While not shown in FIG. 2, it is to be understood that third gas passage 222 may be coupled to a suitable patient delivery mechanism, such as a mouthpiece or endotracheal tube.

A concentration sensor 220 is positioned along second gas passage 230 and third gas passage 222. Concentration sensor 220 includes a concentration sensor inlet 218 and a concentration sensor outlet 224 through which the fresh gas/vaporized anesthetic mix flows. Concentration sensor 220 may be similar to concentration sensor 120 of FIG. 1, and thus the description of concentration sensor 120 likewise applies to concentration sensor 220.

System 299 further includes a controller 260, similar to controller 160 of FIG. 1. Thus, controller 260 includes a processor operatively connected to a memory. The memory may be a non-transitory computer-readable medium and may be configured to store computer executable code (e.g., instructions) to be processed by the processor in order to execute one or more routines as described herein. The memory may also be configured to store data received by the processor.

Controller 260 is configured to receive and process data. Data may be input by a user via a user input device 264 that is operationally connected to the processor and thus is configured to an input signal 262 to controller 260. User input device 264 may be similar to user input device 164 of FIG. 1 and thus the description of user input device 164 likewise applies to user input device 264. Controller 260 may be operatively connected to other computing devices, such as hospital computing devices (e.g., electronic medical record-storing devices, operating room workstations, and/or anesthesia delivery machines).

Controller 260 is configured to receive output from components of system 299. As shown, controller 260 is operably coupled to concentration sensor 220, which sends a concentration signal 236 indicative of a concentration of anesthetic agent in the fresh gas/vaporized anesthetic mix to controller 260.

Controller 260 is configured to process the output received by the input device and sensors and adjust one or more actuators of system 299 in response to the received output. The one or more actuators that may be adjusted by controller 260 include a driver 248 of the heating element of CFV 258 (e.g., the resistive heater of vaporizer 259). For example, controller 260 may send a heater control signal 250 to driver 248 to adjust the current or voltage supplied to the heating element of CFV 258. Further, in some examples, injector 240 may include a controllable valve that may be controlled via an injector control signal from controller 260. The controllable valve may adjusted to titrate a target amount of vaporized anesthetic agent to second gas passage 230.

In this way, a concentration of anesthetic agent in the fresh gas/vaporized anesthetic mix supplied to the patient may be measured from output from concentration sensor 220. The concentration may be used by controller 260 to adjust an amount of current or voltage supplied to the heating element/vaporizer 259 of CFV 258, which results in a change of temperature of vaporizer 259 and hence a change in the amount of liquid agent that is vaporized and supplied to the patient. For example, controller 260 may modulate the electrical power applied to the CFV heating element based on an error signal obtained between the measured and a set anesthetic agent concentration (e.g., user set).

While FIG. 2 illustrates only a single reservoir for housing the liquid anesthetic, the system of FIG. 2 may include more than one reservoir, each housing a different liquid anesthetic agent and coupled to a different CFV, vapor reservoir, and injector. Each injector may be configured to inject a respective anesthetic agent into the fresh gas flow provided by the gas source. In this way, a single anesthetic breathing system may be used to supply different anesthetic agents. In such a configuration, only one CFV may be activated at a given time, and the activated CFV may be controlled based on the concentration of the anesthetic agent being vaporized by the activated CFV, in the manner described above. In some examples, various components of system 299 may be housed in a patient breathing machine, such as anesthesia machine 12 of FIG. 11. For example, vapor reservoir 228 and associated gas passages (e.g., passages 204 and 230), injector 240, controller 260, and sensor 220 may be housed in the patient breathing machine. CFV 258 and liquid anesthetic agent reservoir 256 may be a separate unit, similar to container 30 of FIG. 11, which couples to the patient breathing machine.

Figure 3:
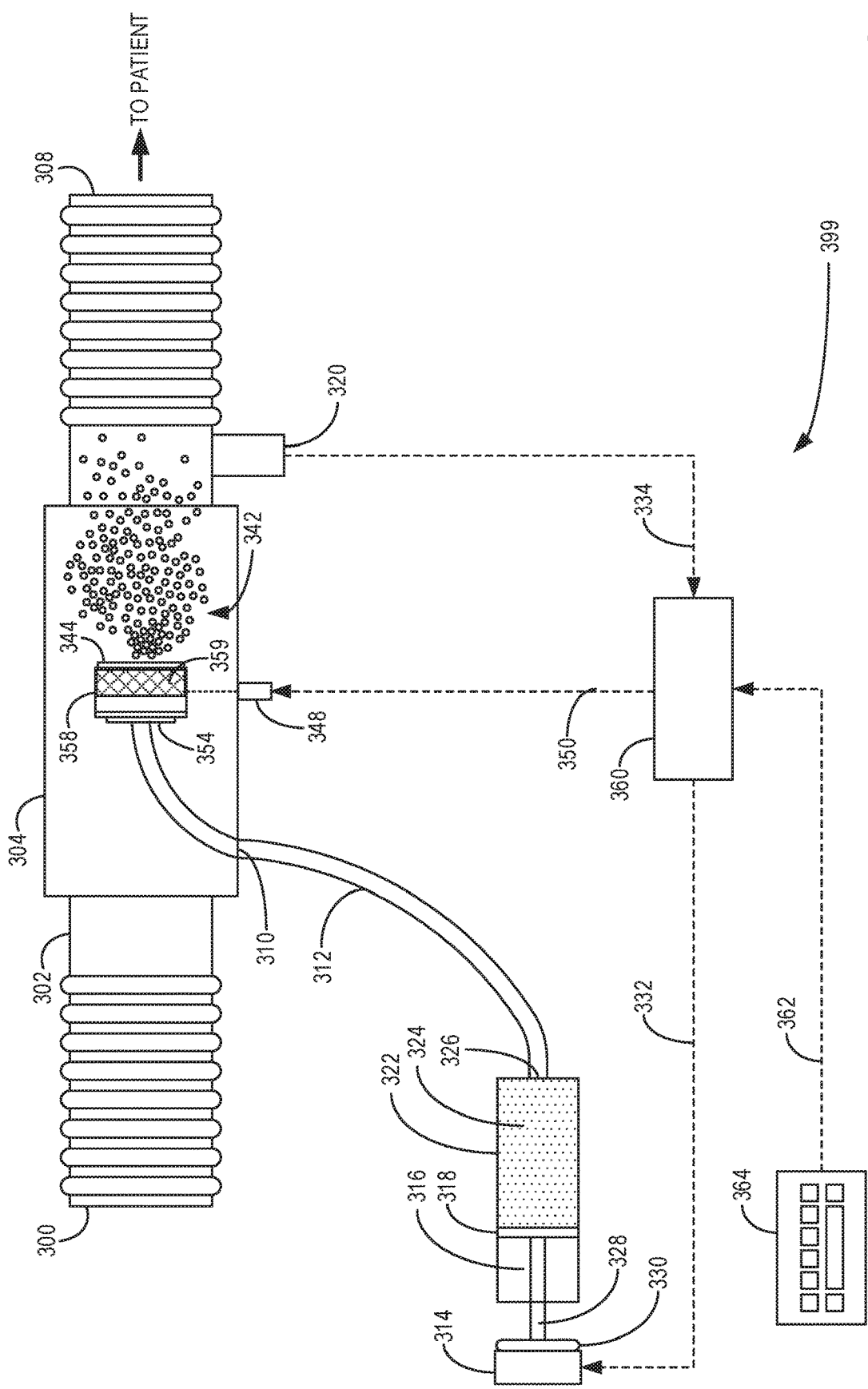
FIG. 3 schematically shows a third embodiment of an anesthetic agent delivery system.

FIG. 3 is a schematic view of an anesthetic delivery system 399 according to a third embodiment of the present disclosure. System 399 may be similar to system 199 of FIG. 1 and system 299 of FIG. 1, but may be a distal direct vapor injection configuration where liquid anesthetic agent or other vaporizable medication/compound is supplied to the CFV via a syringe pump. System 399 includes a gas passage 302. Gas passage 302 includes a first end 300, via which fresh gas (e.g., oxygen, nitrous oxide, and/or fresh air) may enter. The fresh gas may be supplied from a suitable source, such as pipeline, tank, etc. Gas passage 302 further includes a mixing region 304 in which vaporized anesthetic agent is mixed with the fresh gas. The resultant fresh gas/vaporized anesthetic agent mix is supplied to a patient via a second end 308 of gas passage 302. As shown in FIG. 3, gas passage 302 may be a breathing tube configured to be coupled to a mask, tracheal tube, or other suitable breathing circuit component. In this manner, vaporization of the anesthetic agent or other vaporizable medication/compound may be performed proximate the patient or near the patient mask, cannula, or endotracheal tube for mechanically ventilated patients.

Mixing region 304 houses CFV 358, which is fluidically coupled to a syringe pump 322. Syringe pump 322 includes a compression section 324, plunger seal 318, syringe outlet 326, plunger rod 328, plunger handle 330, and plunger actuator 314. Upon actuation of plunger actuator 314, plunger handle 330 moves, thus moving plunger rod 328 and plunger seal 318. Liquid anesthetic agent stored in compression section 324 may then be compressed, urging the liquid anesthetic agent out of outlet 326 and into liquid anesthetic agent passage 312. Liquid anesthetic agent in liquid anesthetic agent passage 312 is supplied to CFV 358 via an opening 310 in mixing region 304, where the anesthetic is vaporized.

CFV 358 includes an inlet 354, a vaporizer 359, and an outlet 344. A heating element of vaporizer 359 vaporizes the anesthetic agent supplied from passage 312, and an amount of liquid anesthetic agent vaporized may be proportional to a temperature of vaporizer 359. Vapor is released from CFV 358 via outlet 344 as a controllable (programmable) vapor flow 342. The vapor flow 342 mixes with the supplied fresh air in mixing region 304 and the fresh gas/vaporized anesthetic agent mix flows to second end 308 of gas passage 302 and ultimately to the patient.

A concentration sensor 320 is positioned along second gas passage 302 downstream of mixing region 304. Concentration sensor 320 may be similar to concentration sensor 120 described above and thus description of concentration sensor 120 likewise applies to concentration sensor 320.

System 399 further includes a controller 360, similar to controller 160 of FIG. 1. Thus, controller 360 includes a processor operatively connected to a memory. The memory may be a non-transitory computer-readable medium and may be configured to store computer executable code (e.g., instructions) to be processed by the processor in order to execute one or more routines as described herein. The memory may also be configured to store data received by the processor.

Controller 360 is configured to receive and process data. Data may be input by a user via a user input device 364 that is operationally connected to the processor and thus is configured to an input signal 362 to controller 360. User input device 364 may be similar to user input device 164 of FIG. 1. Controller 360 may be operatively connected to other computing devices, such as hospital computing devices (e.g., electronic medical record-storing devices, operating room workstations, and/or anesthesia delivery machines).

Controller 360 is configured to receive output from components of system 399. As shown, controller 360 is operably coupled to concentration sensor 320, which sends a concentration signal 334 indicative of a concentration of anesthetic agent in the fresh gas/vaporized anesthetic mix to controller 360.

Controller 360 is configured to process the output received by the user input device and sensors and adjust one or more actuators of system 399 in response to the received output. The one or more actuators that may be adjusted by controller 360 include a driver 348 of the heating element of CFV 358 (e.g., the resistive heater of vaporizer 359) and syringe pump 322. For example, controller 360 may send a heater control signal 350 to driver 348 to adjust the current or voltage supplied to the heating element of CFV 358. Further, controller 360 may send a plunger control signal 332 to plunger actuator 314 to adjust a position of plunger seal 318 and thus an amount of liquid anesthetic agent supplied to CFV 358. As shown in FIG. 3, driver 348 is positioned outside gas passage 302/mixing region 304 and is operably (e.g., electrically) coupled to vaporizer 359. However, other configurations are possible, such as driver 348 being positioned inside mixing region 304.

Figure 4:
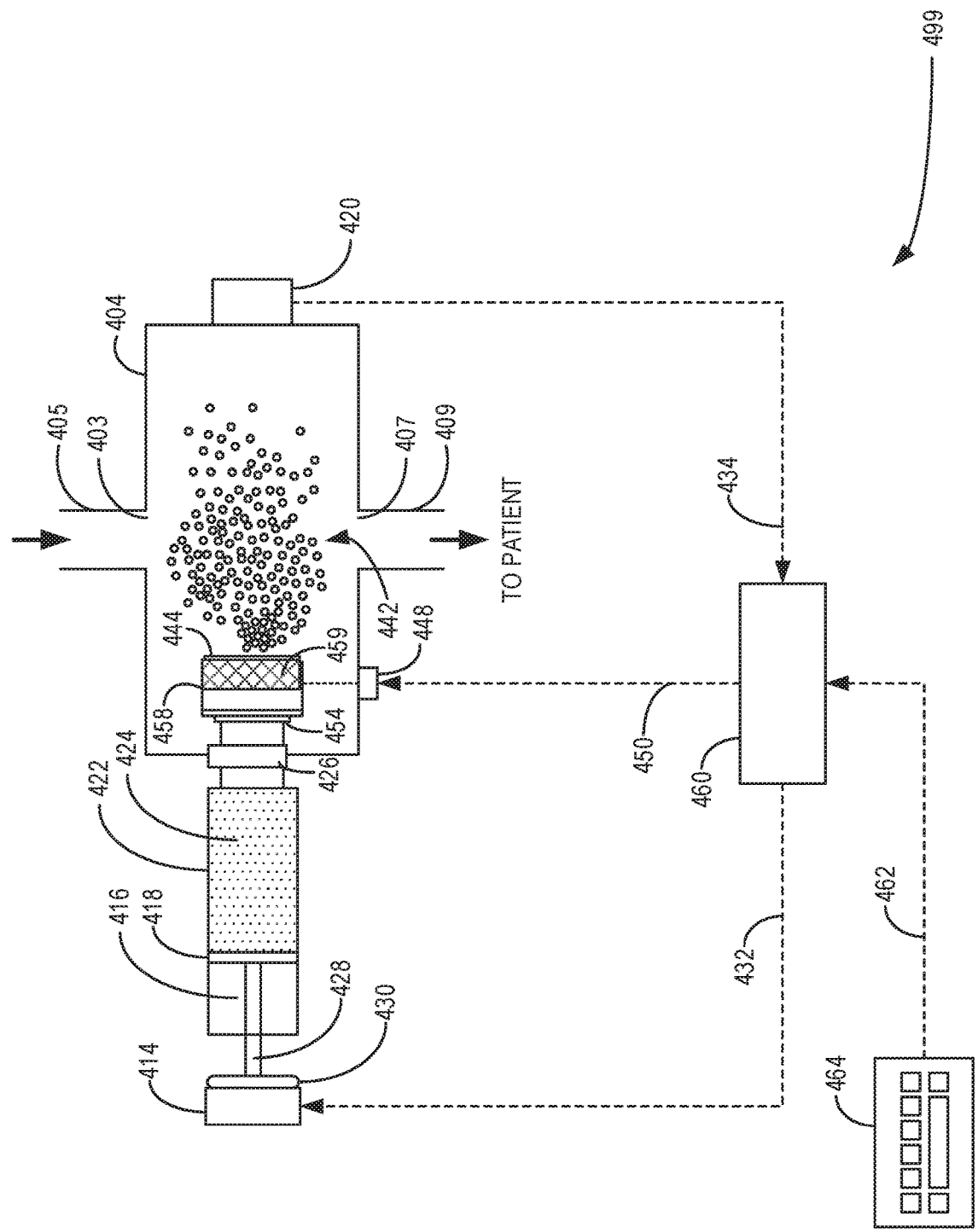
FIG. 4 schematically shows a fourth embodiment of an anesthetic agent delivery system.

FIG. 4 is a schematic view of an anesthetic delivery system 499 according to a fourth embodiment of the present disclosure. System 499 may be similar to system 499 of FIG. 3, but may have a syringe pump directly coupled to vapor mixing region rather than distally coupled as in the configuration of FIG. 3. Thus, system 499 includes a vapor mixing region 404 having an inlet 403 coupled to a gas inlet passage 405, via which fresh gas (e.g., oxygen, nitrous oxide, and/or fresh air) may enter. The fresh gas may be supplied from a suitable source, such as pipeline, tank, etc. Vapor mixing region 404 houses CFV 458 and thus vaporized anesthetic agent is mixed with the fresh gas in vapor mixing region 404. The resultant fresh gas/vaporized anesthetic agent mix is supplied to a patent via an outlet 407 and a gas outlet passage 409. Gas outlet passage 409 may be coupled to a mask, tracheal tube, or other suitable breathing circuit component, either proximally or distally.

CFV 458 is fluidically coupled to a syringe pump 422. Syringe pump 422 includes a compression section 424, plunger seal 418, syringe outlet 426, plunger rod 428, plunger handle 430, and plunger actuator 414. Upon actuation of plunger actuator 414, plunger handle 430 moves, thus moving plunger rod 428 and plunger seal 418. Liquid anesthetic agent stored in compression section 424 may then be compressed, urging the liquid anesthetic agent out of compression section 424 and into CFV 458. Syringe outlet 426 may form a coupling region whereby syringe pump 422 may couple to mixing region 404.

CFV 458 includes an inlet 454, a vaporizer 459, and an outlet 444. A heating element of vaporizer 459 vaporizes the anesthetic agent supplied from syringe pump 422, and an amount of liquid anesthetic agent vaporized may be proportional to a temperature of vaporizer 459. Vapor is released from CFV 458 via outlet 444 as a controllable (programmable) vapor flow 442. The vapor flow 442 mixes with the supplied fresh gas in vapor mixing region 402 and the fresh gas/vaporized anesthetic agent mix flows the patient.

A concentration sensor 420 is positioned at vapor mixing region 402, though other locations are possible (e.g., in a gas passage between vapor mixing region 402 and the patient). Concentration sensor 420 may be similar to concentration sensor 120 described above.

System 499 further includes a controller 460, similar to controller 160 of FIG. 1. Thus, controller 460 includes a processor operatively connected to a memory. The memory may be a non-transitory computer-readable medium and may be configured to store computer executable code (e.g., instructions) to be processed by the processor in order to execute one or more routines as described herein. The memory may also be configured to store data received by the processor.

Controller 460 is configured to receive and process data. Data may be input by a user via a user input device 464 that is operationally connected to the processor and thus is configured to an input signal 462 to controller 460. User input device 464 may be similar to user input device 164 of FIG. 1. Controller 460 may be operatively connected to other computing devices, such as hospital computing devices (e.g., electronic medical record-storing devices, operating room workstations, and/or anesthesia delivery machines).

Controller 460 is configured to receive output from components of system 399. As shown, controller 460 is operably coupled to concentration sensor 420, which sends a concentration signal 434 indicative of a concentration of anesthetic agent in the fresh gas/vaporized anesthetic mix to controller 460.

Controller 460 is configured to process the output received by the user input device and sensors and adjust one or more actuators of system 499 in response to the received output. The one or more actuators that may be adjusted by controller 460 include a driver 448 of the heating element of CFV 458 (e.g., the resistive heater of vaporizer 459) and syringe pump 422. For example, controller 460 may send a heater control signal 450 to driver 448 to adjust the current or voltage supplied to the heating element of CFV 458. Further, controller 460 may send a plunger control signal 432 to plunger actuator 414 to adjust a position of plunger seal 418 and thus an amount of liquid anesthetic agent supplied to CFV 458.

Thus, the systems described above with respect to FIGS. 3 and 4 include a syringe pump to supply liquid anesthetic agent to a CFV. The syringe pumps may be manufactured with desired anesthetic agent present in a respective compression section, such that at least some portions of the syringe pumps may be single use. By providing the anesthetic agent in a single-use format, refilling of an anesthetic agent reservoir in a clinical environment (e.g., operating room) may be avoided, reducing health and environmental hazards associated with exposure to anesthetic agents. Further, contamination of the anesthetic agents during refill may be avoided. Additionally, eliminating reservoir refill may also reduce the cost, complexity, and space to accommodate custom/keyed filler apparatus. Further, in some examples, the systems of FIGS. 3 and/or 4 may be used to deliver medication other than anesthetic agent, such as for pain relief, anti-nausea, anti-seizure, anti-migraine, etc. For example, controller 460 may be operatively configured to dispense a non-anesthetic, vaporizable medication at specified intervals as determined by an appropriate clinician (e.g., physician, respiratory therapist) for an ICU patient via a non-rebreathing mask, intubated airway, etc., downstream of gas outlet passage 409. Alternatively, the device may be configured to deliver pain relieving medication upon patient demand. The heated vaporized medication delivery described herein may deliver the desired drug without thermal degradation, by rapidly heating a thin film liquid layer of the drug at the interface between the capillary member and the heating element of the vaporizer. As a non-limiting example, system 499 may be effectively separated between structure 404 (e.g., which may be housed within a ventilatory device) and syringe pump 422. The mixing region 404 may be fitted with a user-accessible quick-connect valve interposed between the syringe pump 422 and mixing region 404. A one-way valve may fluidically couple syringe pump 422 and the CFV 458. Likewise, in the system 399 of FIG. 3, a the syringe pump may be used to deliver anesthetics/medication in the condition that the ventilator device does not contain the infrastructure to support direct syringe delivery, as illustrated and previously described in FIG. 4.

Figure 5:
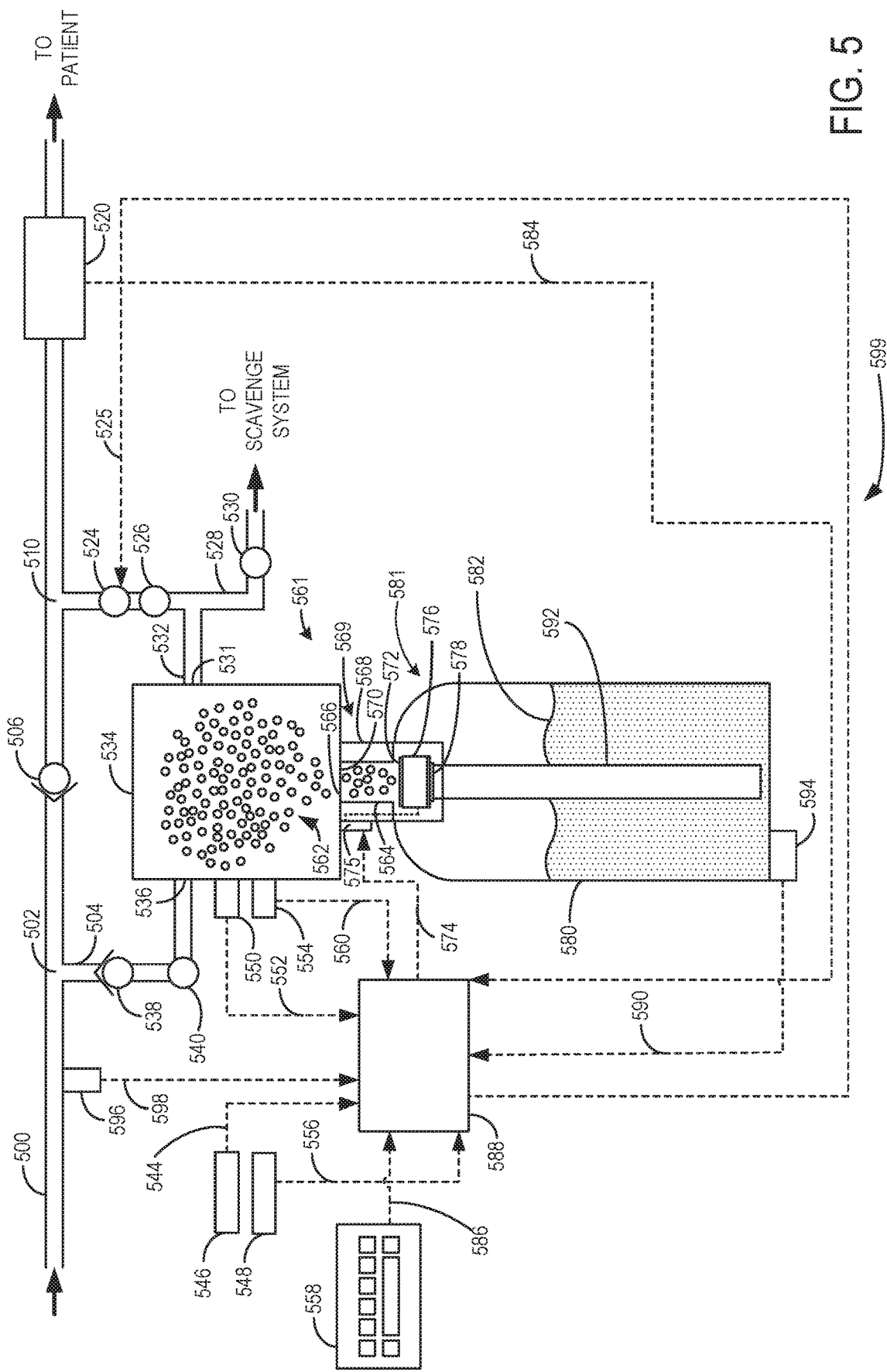
FIG. 5 schematically shows a fifth embodiment of an anesthetic agent delivery system.
Figure 6:
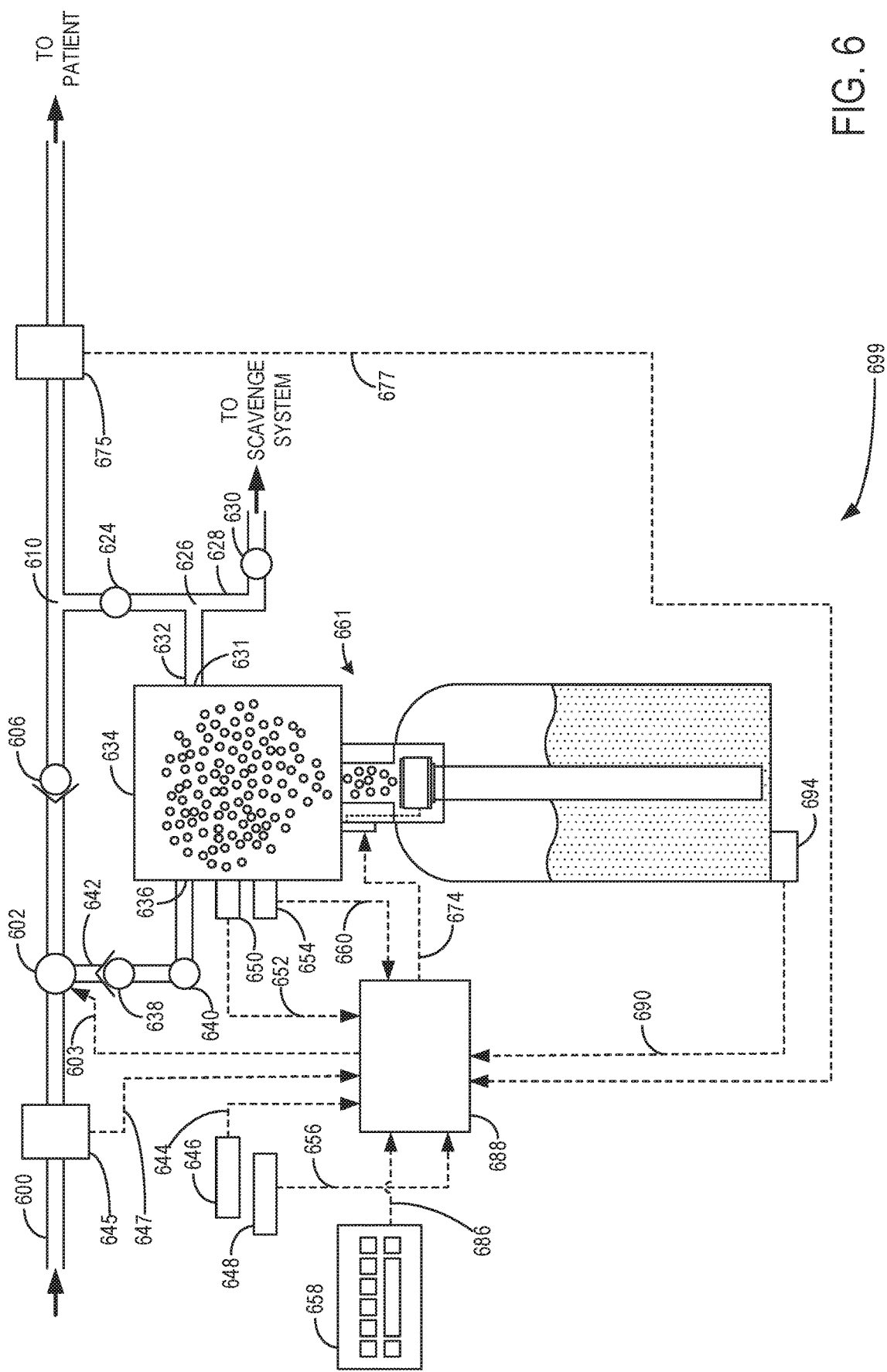
FIG. 6 schematically shows a sixth embodiment of an anesthetic agent delivery system.
Figure 7:
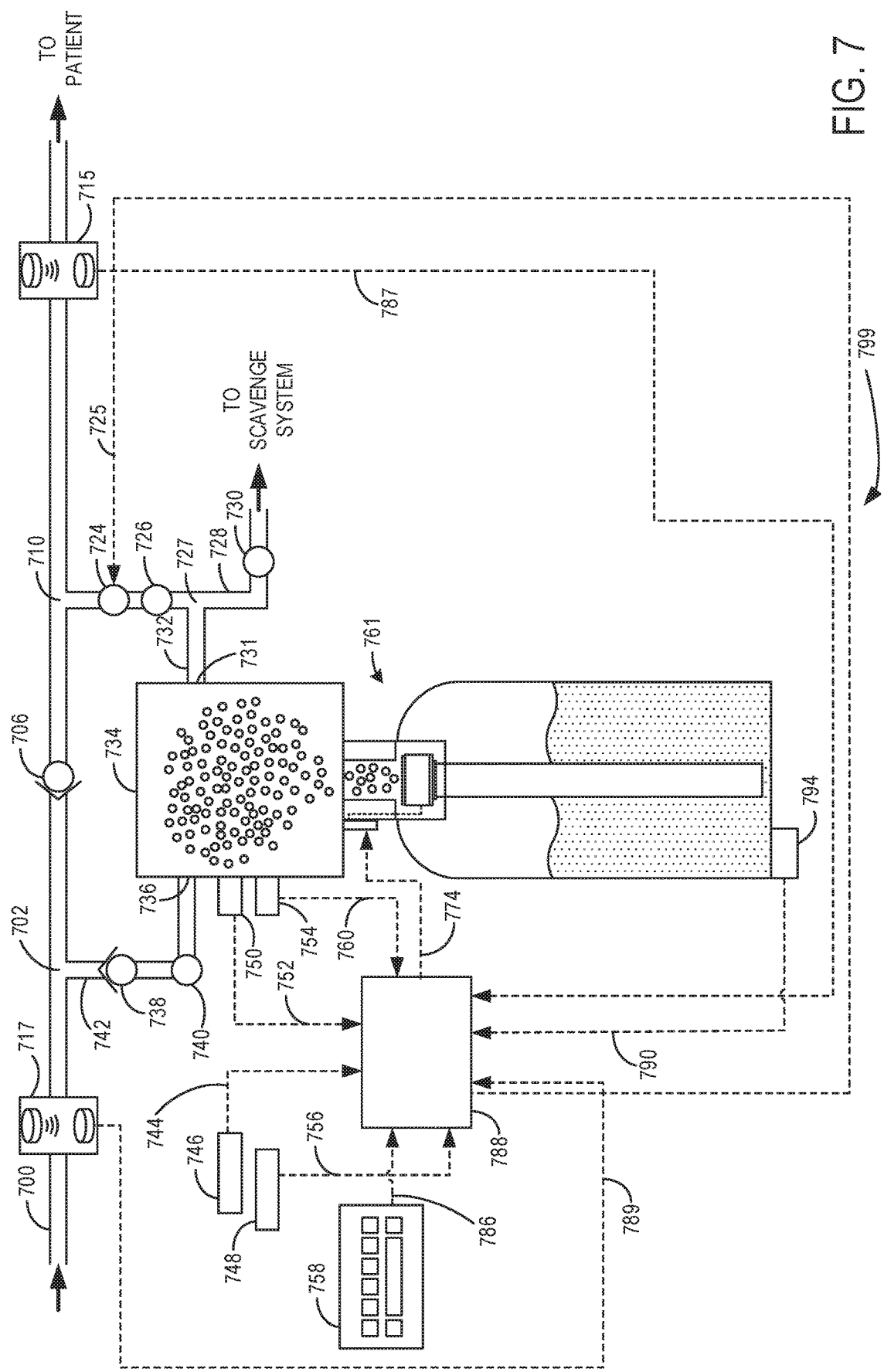
FIG. 7 schematically shows a seventh embodiment of an anesthetic agent delivery system.

Turning now to FIGS. 5-7, embodiments of anesthetic agent delivery systems whereby a drug bottle is used as a combined anesthetic reservoir and delivery device are shown. For example, the anesthetic agent may be manufactured/packaged in a bottle that includes a CFV or the anesthetic agent may be manufactured/packaged in a bottle that is adapted to couple to an adapter including a CFV.

Utilizing a drug bottle as a combined anesthetic reservoir and delivery device may provide multiple advantages. For example, the anesthetic agent remains sealed for an entirety of its service life, preventing contents of the bottle from contamination. Further, as explained above, such a configuration eliminates the need for a user to re-fill vaporizers, as a new bottle is inserted instead. In this way, accidental spill of agent from the bottle during normal filling process of existing vaporizers may be avoided, along with user exposure hazard during fill/use. In some examples, the entire bottle and delivery device (e.g., CFV) may be disposable, further reducing the risk for user exposure. Further still, the reliability of the vaporizer element may now be measured in terms of hours/days/weeks rather than years, if the CFV is made disposable with bottle. For example, current vaporizers may accumulate plasticizer byproducts (such as butylated hydroxytoluene) over their lifetime (10+ years) which are extracted from the wetted materials used in the construction of the vaporizer, which can affect the performance of the vaporizer and perhaps the delivery of the drug. In contrast, the self-contained integrated bottle/CFV unit does not suffer from such issues, as the bottle along with the integral vaporizer is discarded once the liquid in the bottle is consumed. Additionally, such a configuration may ease anesthetic agent delivery in the ICU or military field, for example by allowing for use of the bottle/CFV with a ventilator rather than an anesthesia machine.

Referring first to FIG. 5, it shows a schematic view of an anesthetic delivery system 599 according to a fifth embodiment of the present disclosure. System 599 is configured similarly to a bypass vaporizing system, where fresh gas is split into carrier gas that mixes with vaporized anesthetic agent in a vapor reservoir and bypass gas that bypasses the vapor reservoir. System 599 includes a combined liquid anesthetic agent bottle and CFV unit and further includes various sensors and actuators that allow precise control over the concentration of anesthetic agent delivered to a patient.

Fresh gas is provided to system 599 from a gas source (e.g., pipes, tanks, etc.) via gas passage 500. At junction 502, the fresh gas is split into carrier gas and bypass gas. The carrier gas is fed into vapor reservoir 534 via an inflow passage 504. Inflow passage 504 is coupled to vapor reservoir 534 at vapor reservoir gas inlet 536. To prevent backflow of vaporized anesthetic agent, an inflow check valve 538 may be present in inflow passage 504. Further, an inflow valve 540 may be present in inflow passage 504. Inflow valve 540 may be an on/off valve. In one example, during operation of system 599 (e.g., when the CFV is activated and anesthetic agent is supplied to the patient), inflow valve 540 may be open to allow flow of carrier gas into vapor reservoir 534, and may be closed only during certain conditions, such as when charging vapor reservoir 534 with vaporized anesthetic agent. For example, if the pressure within the agent reservoir 534, as measured by reservoir pressure sensor 550, is above the pressure of the incoming fresh gas in gas passage 500, as measured by fresh gas pressure sensor 596, valve 540 is closed and all fresh gas may be routed directly to the patient without traveling through vapor reservoir 534 while agent vapor is metered out of the pressurized agent reservoir 534 via proportional valve 524, until which time the pressure within agent reservoir 534 is at the same or lower pressure than the pressure of the fresh gas as measured by sensor 596. Likewise, if reservoir pressure sensor 550 measures a pressure below the pressure of the fresh gas, some fresh gas is routed through vapor reservoir 534 where the fresh gas picks up agent vapor. The remaining fresh gas passes through the valve 506 to the patient. In another example, inflow valve 540 may be a normally-closed valve in order to maintain a concentration of vaporized anesthetic agent in vapor reservoir 534 at 100% whereby the outflow of agent from the vaporizer reservoir 534 is controlled via a purposefully designed venturi effect at junction 510 and outflow proportional valve 524. In such a configuration, inflow valve 540 may be opened during certain conditions to allow the carrier gas into vapor reservoir 534, such as when system 599 is deactivated (e.g., when the CFV is turned off and anesthetic agent is no longer supplied to the patient, in order to flush vaporized anesthetic agent out of vapor reservoir 534 and outflow valve 526).

Vaporized anesthetic agent in vapor reservoir 534 (and in some examples, a mix of carrier gas and vaporized anesthetic agent) is flushed out of the vapor reservoir 534 at vapor reservoir gas outlet 531 to outflow passage 532. Outflow passage 532 couples to gas passage 500 at junction 510, where the vaporized anesthetic agent mixes with the bypass gas (e.g., fresh gas). This mixture of fresh gas and vaporized anesthetic agent is eventually supplied to a patient. As shown in FIG. 5, gas passage 500 further includes a back-pressure regulator and/or check valve 506 intermediate junction 502 and junction 510 to prevent backflow of vaporized anesthetic agent in gas passage 500. Further, the flow rate of vaporized anesthetic agent and carrier gas may be controlled by proportional valve 524 positioned in outflow passage 532.

System 599 further includes a routing to a scavenge system configured to scavenge waste anesthetic agent (e.g., vaporized anesthetic agent that is mixed with carrier gas but not ultimately supplied to the patient). As such, outflow passage 532 is coupled to scavenge gas passage 528, which is coupled on its downstream end to a scavenge system. The scavenge system may absorb or otherwise remove anesthetic agent from the carrier gas/anesthetic agent mix via an absorbent material such as charcoal or release the carrier gas/anesthetic agent mixture into an external environment. The supply of waste anesthetic agent in passage 528 to the scavenge system may be controlled by scavenge valve 530. For example, when the CFV is shut off and anesthetic agent is no longer supplied to the patient, scavenge valve 530 may be opened to allow flow of vaporized anesthetic agent to the scavenge system. Further, an outflow valve 526 may be positioned in outflow passage 532. Outflow valve 526 may be a type of shuttle valve, wherein in its first position, the output from outflow passage 532 is pneumatically occluded (e.g., sealing vapor reservoir 534 from junction 510). In its second position, the pneumatic connection between the vapor reservoir 534 and junction 510 is established, and in its third position, a pneumatic connection between vapor reservoir 534 and the scavenging system (e.g., via passage 528) is obtained.

Vaporized anesthetic agent is supplied to vapor reservoir 534 from an anesthetic agent container/CFV unit 561. As shown, the anesthetic agent container/CFV unit 561 includes a liquid anesthetic agent container 580 including a base region 581 housing liquid anesthetic 582 and an adapter region 569 including an adapter 568 housing a CFV 576. In one example, anesthetic agent container/CFV unit 561 may be supplied in its entirety from a manufacturer of the liquid anesthetic agent. In such a configuration, at the time of initial use of anesthetic agent container/CFV unit 561, an operator may couple anesthetic agent container/CFV unit 561 to vapor reservoir 534 via suitable a fastening mechanism, such as a threaded screw-type fastener (e.g., where a coupling end located at the top of adapter 568 is inserted into a coupling end located at the bottom of vapor reservoir 534 and anesthetic agent container/CFV unit 561 is rotated to engage threads on the coupling end of adapter 568 with threads on vapor reservoir 534). In other examples, liquid anesthetic agent container 580 may be supplied from a manufacturer separately from adapter 568 and/or CFV 576. For example, adapter 568 (including CFV 576) may be fixed to vapor reservoir 534. At the time of initial use of liquid anesthetic agent container 580, an operator may couple liquid anesthetic agent container 580 to adapter 568 via a suitable fastening mechanism. In either case, liquid anesthetic agent container 580 may be a non-refillable, single-use, disposable container that is not pressurized by an external pressure source.

In configurations where the CFV and filled bottle are sold together as a single unit, the heating element driver 575 may be packaged in the anesthesia machine. In a non-limiting example, the electrical power connection to the heating element of the CFV may be established by use of spring loaded contacts or blind mate connector. In an additional non-limiting example, the bottle/CFV unit may both pneumatically seal and hydraulically couple via a quarter turn or push-to-connect fitting. In a still further example, an all-in-one connector (e.g., pneumatic seal with hydraulic coupling with integral electrical connection) may be used.

Adapter 568 houses CFV 576. CFV 576 is similar to CFV 158 of FIG. 1, and thus description of CFV 158 likewise applies to CFV 576, and as such includes a vaporizer/heating element and a wick 592 that extends into liquid anesthetic agent container 580. When anesthetic agent container/CFV unit 561 is coupled to vapor reservoir 534, adapter 568 may be fluidically coupled to vapor reservoir 534 via adapter outlet 570, which couples to vapor reservoir 534 at reservoir vapor inlet 566. Adapter outlet 570 is an outlet of adapter vapor passage 564, which fluidically couples to an interior of liquid anesthetic agent container 580. During use, liquid anesthetic agent is drawn up wick 592 and into CFV 576 at inlet 578 via capillary action and is vaporized by the heating element of CFV 576, resulting in a vapor flow 562 that exits CFV 576 at outlet 572 and enters vapor reservoir 534 via adapter vapor passage 564, adapter outlet 570, and reservoir vapor inlet 566. A driver 575 (which may be external to the CFV; e.g., on the system side of the reservoir assembly) is also present to control a temperature of the heating element.

System 599 further includes a controller 588. Controller 588 is similar to controller 160 of FIG. 1 and as such includes a processor operatively connected to a memory. The memory may be a non-transitory computer-readable medium and may be configured to store computer executable code (e.g., instructions) to be processed by the processor in order to execute one or more routines as described herein. The memory may also be configured to store data received by the processor.

Controller 588 is configured to receive and process data. Data may be input by a user via a user input device 558 (similar to user input device 164 of FIG. 1) that is operationally connected to the processor and thus is configured to an input signal 586 to controller 588. Controller 588 may be operatively connected to other computing devices, such as hospital computing devices (e.g., electronic medical record-storing devices, operating room workstations, and/or anesthesia delivery machines).

Controller 588 is configured to receive output from a plurality of sensors of system 599. As shown, controller 588 is operably coupled to a concentration sensor 520, which sends a concentration signal 584 indicative of a concentration of anesthetic agent in the fresh gas/vaporized anesthetic mix within gas passage 500 (downstream of junction 510) to controller 588. Additional sensors operatively coupled to controller 588 include ambient pressure sensor 546 (configured to send an ambient pressure signal 544 to controller 588 indicative of a pressure of the environment surrounding system 599), ambient temperature sensor 548 (configured to send an ambient temperature signal 556 to controller 588 indicative of a temperature of the environment surrounding system 599), fresh gas pressure sensor 596 (configured to send a fresh gas pressure signal 598 to controller 588 indicative of a pressure of fresh gas 500), reservoir pressure sensor 550 (configured to send a reservoir pressure signal 552 to controller 588 indicative of a pressure of vapor reservoir 534), reservoir temperature sensor 554 (configured to send a reservoir temperature signal 560 to controller 588 indicative of a temperature of vapor reservoir 534), and fluid level sensor 594 (configured to send a fluid level signal 590 to controller 588 indicative of a level of liquid anesthetic agent in liquid anesthetic container 580).

Controller 588 is configured to process the output received by the input device and sensors and adjust one or more actuators of system 599 in response to the received output. The one or more actuators that may be adjusted by controller 588 include driver 575 of the heating element of CFV 576 (driver may be external to the CFV; e.g., on the system side of the reservoir assembly), inflow valve 540, outflow valve 526, proportional valve 524, and scavenge valve 530. For example, controller 588 may send a heater control signal 574 to driver 575 to adjust the current or voltage supplied to the heating element of CFV 576. In an example, controller 588 may send a proportional valve signal 525 to proportional valve 524 to adjust a position of proportional valve 524. Additionally, controller 588 may be configured to display information and/or otherwise notify an operator of system 599 of various conditions of system 599, such as the level of liquid anesthetic agent in liquid anesthetic agent container 580.

Thus, at least in one example, a liquid anesthetic agent container may include an integrated CFV. For example, as shown in FIG. 11, the container 30 may include a base region 31, where an interior of the base region holds liquid anesthetic agent. The container may also include an adapter region 33. In one example, the adapter region may form the neck of the liquid anesthetic agent container and may be continuous with the base region. A capillary force vaporizer (CFV) may be housed in the adapter region, and the adapter region may include a coupling end configured to couple to a patient breathing circuit, such as anesthesia machine 12 of FIG. 11, in order to supply anesthetic agent vaporized by the CFV to a patient. The patient breathing circuit may include an anesthesia machine or ventilator, along with associated componentry (e.g., gas/breathing passages to supply the fresh gas/anesthetic agent mix to a patient, scavenge system, coupling to a gas source). For example, the coupling end of the unit 561 (e.g., adapter 568) may be similar to coupling end 32 of container 30 of FIG. 11 and thus connect to a port of the anesthesia machine (e.g., port 22 of FIG. 11) to supply vaporized anesthetic agent to the anesthesia machine (e.g., to vapor reservoir 20 of FIG. 11).

The coupling end may include a fastener configured to couple to a complementary fastener of the patient breathing circuit. For example, the anesthesia machine may house the vapor reservoir illustrated in FIG. 5, and the anesthesia machine may include a port (e.g., port 22 of FIG. 11) that includes the complementary fastener (e.g., complementary fastener 23 of FIG. 11). The adapter region may be configured to couple to the port, such that when coupled, the anesthetic agent vaporized by the CFV is configured to flow to a gas passage of the anesthesia machine.

The adapter region may further include an electrical connection configured to electrically couple the CFV to a controller of the anesthesia machine (or ventilator). For example, driver 575 may be housed in the anesthesia machine and may couple to CFV 576 via an electrical connection (e.g., via a first electrical connector of the unit and a second electrical connector of the anesthesia machine, such as via connectors 24 and 34 of FIG. 11). The CFV includes a heating element and a wick, and the wick extends into the interior of the liquid anesthetic agent container. The liquid anesthetic agent in the container may travel along the wick via capillary action and be supplied to the heating element, where the agent is vaporized. The electrical connection may be configured to electrically couple the heating element to the controller of the anesthesia machine via a driver, and the controller may be configured to modulate the temperature of the heating element to regulate the amount of agent that is vaporized. The container may further include a liquid level sensor configured to measure a level of liquid anesthetic agent in the liquid anesthetic agent container. The liquid level sensor may be wirelessly coupled to the controller or another suitable device, so that an operator may be notified when the liquid anesthetic level is below a threshold. The operator may then remove the container and integrated CFV and insert a new container (pre-filled with liquid anesthetic agent) into the breathing circuit (e.g., anesthesia machine), establishing connection between the CFV and controller as well as connection between the CFV and vapor reservoir/gas passages of the breathing circuit/anesthesia machine.

Referring next to FIG. 6, it shows a schematic view of an anesthetic delivery system 699 according to a sixth embodiment of the present disclosure. System 699 is configured similarly system 599 of FIG. 5, and as such is a bypass vaporizing system, where fresh gas is split into carrier gas that mixes with vaporized anesthetic agent in a vapor reservoir and bypass gas that bypasses the vapor reservoir. System 699 includes a combined liquid anesthetic agent bottle and CFV unit and further includes various sensors and actuators that allow precise control over the concentration of anesthetic agent delivered to a patient. However, rather than including a concentration sensor for control over the heating element of the CFV, system 699 includes dual mass flow sensors, which may reduce costs relative to the use of the concentration sensor.

Fresh gas is provided to system 699 from a gas source (e.g., pipes, tanks, etc.) via gas passage 600. A multi-outlet valve 602 is positioned at a junction between gas passage 600 and inflow passage 642. The fresh gas is split into carrier gas and bypass gas at multi-outlet valve 602. The carrier gas is fed into vapor reservoir 634 via inflow passage 642. Inflow passage 642 is coupled to vapor reservoir 634 at vapor reservoir gas inlet 636. To prevent backflow of vaporized anesthetic agent, an inflow check valve 638 may be present in inflow passage 642. Further, an inflow valve 640 may be present in inflow passage 642. Inflow valve 640 may be a normally-open valve to allow carrier gas to flow into vapor reservoir 634. Inflow valve 640 may be closed during certain conditions, such as when charging vapor reservoir 634 with vaporized anesthetic agent and/or when the CFV is deactivated and anesthetic agent is no longer supplied to the patient.

The carrier gas mixes with vaporized anesthetic agent in vapor reservoir 634 and the mix of carrier gas (e.g., fresh gas) and vaporized anesthetic agent is pushed out of the vapor reservoir 634 at vapor reservoir gas outlet 631 to outflow passage 632. Outflow passage 632 couples to gas passage 600 at junction 610, where the mix of fresh gas and vaporized anesthetic agent mixes with the bypass gas (e.g., fresh gas). This mixture of bypass gas, carrier gas, and vaporized anesthetic agent is eventually supplied to a patient. As shown in FIG. 6, gas passage 600 further includes a back-pressure regulator and/or check valve 606 intermediate multi-outlet valve 602 and junction 610 to prevent backflow of vaporized anesthetic agent in gas passage 600.

System 699 further includes a routing to a scavenge system configured to scavenge waste anesthetic agent (e.g., vaporized anesthetic agent that is mixed with carrier gas but not ultimately supplied to the patient). As such, outflow passage 632 is coupled to scavenge gas passage 628 at junction 626, and scavenge gas passage 628 is coupled on its downstream end to a scavenge system, similar to the scavenge system described above with respect to FIG. 5. The supply of waste carrier gas/anesthetic agent mix in passage 628 to the scavenge system may be controlled by scavenge valve 630, e.g., scavenge valve may be normally closed but may be opened when the CFV is deactivated and anesthetic agent is no longer supplied to the patient. Outflow valve 624 may be a type of shuttle valve, wherein in its first position, the output from outflow passage 632 is pneumatically occluded (e.g., sealing vapor reservoir 634 from junction 610). In its second position, the pneumatic connection between the vapor reservoir 634 and junction 610 is established, and in its third position, a pneumatic connection between vapor reservoir 634 and the scavenging system (e.g., via passage 628) is obtained.

Vaporized anesthetic agent is supplied to vapor reservoir 634 from an anesthetic agent container/CFV unit 661. Anesthetic agent container/CFV unit 661 is similar to anesthetic agent container/CFV unit 561 of FIG. 5, and as such includes a CFV that has a heating element driven by a driver, a wick extending into a liquid anesthetic agent container, an adapter, etc. Thus, the description of anesthetic agent container/CFV unit 561 likewise applies to anesthetic agent container/CFV unit 661 and additional description is dispensed with.

System 699 further includes a controller 688. Controller 688 is similar to controller 160 of FIG. 1 and controller 588 of FIG. 5 and as such includes a processor operatively connected to a memory. The memory may be a non-transitory computer-readable medium and may be configured to store computer executable code (e.g., instructions) to be processed by the processor in order to execute one or more routines as described herein. The memory may also be configured to store data received by the processor.

Controller 688 is configured to receive and process data. Data may be input by a user via a user input device 658

(similar to user input device 164 of FIG. 1) that is operationally connected to the processor and thus is configured to an input signal 686 to controller 688. Controller 688 may be operatively connected to other computing devices, such as hospital computing devices (e.g., electronic medical record-storing devices, operating room workstations, and/or anesthesia delivery machines).

Controller 688 is configured to receive output from a plurality of sensors of system 699. As shown, controller 688 is operably coupled to a first mass flow sensor 645, which sends a first mass flow signal 647 to controller 688 indicative of a mass flow rate of fresh gas within gas passage 600 upstream of multi-outlet valve 602. Controller 688 is operably coupled to a second mass flow sensor 675, which sends a second mass flow signal 677 to controller 688 indicative of a mass flow rate of fresh gas within gas passage 600 downstream of junction 610. Additional sensors operatively coupled to controller 688 include ambient pressure sensor 646 (configured to send an ambient pressure signal 644 to controller 688 indicative of a pressure of the environment surrounding system 699), ambient temperature sensor 648 (configured to send an ambient temperature signal 656 to controller 688 indicative of a temperature of the environment surrounding system 699), reservoir pressure sensor 650 (configured to send a reservoir pressure signal 652 to controller 688 indicative of a pressure of vapor reservoir 634), reservoir temperature sensor 654 (configured to send a reservoir temperature signal 660 to controller 688 indicative of a temperature of vapor reservoir 634), and fluid level sensor 694 (configured to send a fluid level signal 690 to controller 688 indicative of a level of liquid anesthetic agent in the liquid anesthetic container of anesthetic agent container/CFV unit 661).

Controller 688 is configured to process the output received by the input device and sensors and adjust one or more actuators of system 699 in response to the received output. The one or more actuators that may be adjusted by controller 688 include a driver of the heating element of the CFV of anesthetic agent container/CFV unit 661, inflow valve 640, outflow valve 624, multi-outlet valve 602, and scavenge valve 630. For example, controller 688 may send a heater control signal 674 to the driver of anesthetic agent container/CFV unit 661 to adjust the current or voltage supplied to the heating element of anesthetic agent container/CFV unit 661. As another example, controller 688 may send a valve signal 603 to multi-outlet valve 602 to adjust a position of multi-outlet valve 602. Additionally, controller 688 may be configured to display information and/or otherwise notify an operator of system 699 of various conditions of system 699, such as the level of liquid anesthetic agent in liquid anesthetic agent container.

Referring now to FIG. 7, it shows a schematic view of an anesthetic delivery system 799 according to a seventh embodiment of the present disclosure. System 799 is configured similarly to system 599 of FIG. 5 and to system 699 of FIG. 6, and as such is a bypass vaporizing system, where fresh gas is split into carrier gas that mixes with vaporized anesthetic agent in a vapor reservoir and bypass gas that bypasses the vapor reservoir. System 799 includes a combined liquid anesthetic agent bottle and CFV unit and further includes various sensors and actuators that allow precise control over the concentration of anesthetic agent delivered to a patient. However, rather than including a concentration sensor or mass flow sensors for control over the heating element of the CFV, system 799 includes ultrasonic sensing system.

Fresh gas is provided to system 799 from a gas source (e.g., pipes, tanks, etc.) via gas passage 700. At a junction 702, the fresh gas is split into carrier gas and bypass gas. The carrier gas is fed into vapor reservoir 734 via inflow passage 742. Inflow passage 742 is coupled to vapor reservoir 734 at vapor reservoir gas inlet 736. To prevent backflow of vaporized anesthetic agent, an inflow check valve 738 may be present in inflow passage 742. Further, an inflow valve 740 may be present in inflow passage 742. Inflow valve 740 may be controlled similarly to inflow valve 540 of FIG. 5.

The carrier gas mixes with vaporized anesthetic agent in vapor reservoir 734 and the mix of carrier gas (e.g., fresh gas) and vaporized anesthetic agent is pushed out of the vapor reservoir 734 at vapor reservoir gas outlet 731 to outflow passage 732. Outflow passage 732 couples to gas passage 700 at junction 710, where the mix of fresh gas and vaporized anesthetic agent mixes with the bypass gas (e.g., fresh gas). This mixture of bypass gas, carrier gas, and vaporized anesthetic agent is eventually supplied to a patient. As shown in FIG. 7, gas passage 700 further includes a back-pressure regulator and/or check valve 706 intermediate junction 702 and junction 710 to prevent backflow of vaporized anesthetic agent in gas passage 700. Further, the flow rate of vaporized anesthetic agent and carrier gas may be controlled by proportional valve 524 positioned in outflow passage 732.

System 799 further includes a routing to a scavenge system configured to scavenge waste anesthetic agent (e.g., vaporized anesthetic agent that is mixed with carrier gas but not ultimately supplied to the patient). As such, outflow passage 732 is coupled to scavenge gas passage 728 at junction 727, and scavenge gas passage 728 is coupled on its downstream end to a scavenge system, similar to the scavenge system described above with respect to FIG. 5. The supply of waste anesthetic agent in passage 728 to the scavenge system may be controlled by scavenge valve 730. For example, when the CFV is shut off and anesthetic agent is no longer supplied to the patient, scavenge valve 730 may be opened to allow flow of vaporized anesthetic agent to the scavenge system. Outflow valve 726 may be a type of shuttle valve, wherein in its first position, the output from outflow passage 732 is pneumatically occluded (e.g., sealing vapor reservoir 734 from junction 710). In its second position, the pneumatic connection between the vapor reservoir 734 and junction 710 is established, and in its third position, a pneumatic connection between vapor reservoir 734 and the scavenging system (e.g., via passage 728) is obtained.

Vaporized anesthetic agent is supplied to vapor reservoir 734 from an anesthetic agent container/CFV unit 761. Anesthetic agent container/CFV unit 761 is similar to anesthetic agent container/CFV unit 561 of FIG. 5, and as such includes a CFV that has a heating element driven by a driver, a wick extending into a liquid anesthetic agent container, an adapter, etc. Thus, the description of anesthetic agent container/CFV unit 561 likewise applies to anesthetic agent container/CFV unit 761 and additional description is dispensed with.

System 799 further includes a controller 788. Controller 788 is similar to controller 160 of FIG. 1 and controller 588 of FIG. 5 and as such includes a processor operatively connected to a memory. The memory may be a non-transitory computer-readable medium and may be configured to store computer executable code (e.g., instructions) to be processed by the processor in order to execute one or more routines as described herein. The memory may also be configured to store data received by the processor.

Controller 788 is configured to receive and process data. Data may be input by a user via a user input device 758 (similar to user input device 164 of FIG. 1) that is operationally connected to the processor and thus is configured to an input signal 786 to controller 788. Controller 788 may be operatively connected to other computing devices, such as hospital computing devices (e.g., electronic medical record-storing devices, operating room workstations, and/or anesthesia delivery machines).

Controller 788 is configured to receive output from a plurality of sensors of system 799. As shown, controller 788 is operably coupled to a first ultrasonic sensor 717, which sends a first ultrasonic signal 789 to controller 788 indicative of a speed of sound of the fresh gas flow upstream of junction 702. Controller 788 is also operably coupled to a second ultrasonic sensor 715, which sends a second ultrasonic signal 787 to controller 788 indicative of a speed of sound of the fresh gas/vaporized anesthetic agent mix in gas passage 700 downstream of junction 710. By determining the difference between the first ultrasonic signal and the second ultrasonic signal, a concentration of vaporized anesthetic agent may be determined.

Additional sensors operatively coupled to controller 788 include ambient pressure sensor 746 (configured to send an ambient pressure signal 744 to controller 788 indicative of a pressure of the environment surrounding system 799), ambient temperature sensor 748 (configured to send an ambient temperature signal 756 to controller 788 indicative of a temperature of the environment surrounding system 799), reservoir pressure sensor 750 (configured to send a reservoir pressure signal 752 to controller 788 indicative of a pressure of vapor reservoir 734), reservoir temperature sensor 754 (configured to send a reservoir temperature signal 760 to controller 788 indicative of a temperature of vapor reservoir 734), and fluid level sensor 794 (configured to send a fluid level signal 790 to controller 788 indicative of a level of liquid anesthetic agent in the liquid anesthetic container of anesthetic agent container/CFV unit 761).

Controller 788 is configured to process the output received by the input device and sensors and adjust one or more actuators of system 799 in response to the received output. The one or more actuators that may be adjusted by controller 788 include a driver of the heating element of the CFV of anesthetic agent container/CFV unit 761, proportional valve 724, inflow valve 740, outflow valve 726, and scavenge valve 730. For example, controller 788 may send a heater control signal 774 to the driver of anesthetic agent container/CFV unit 761 to adjust the current or voltage supplied to the heating element of anesthetic agent container/CFV unit 761. As another example, controller 788 may send a proportional valve signal 725 to proportional valve 724 to adjust a position of proportional valve 724. Additionally, controller 788 may be configured to display information and/or otherwise notify an operator of system 799 of various conditions of system 799, such as the level of liquid anesthetic agent in liquid anesthetic agent container.

Figure 8:
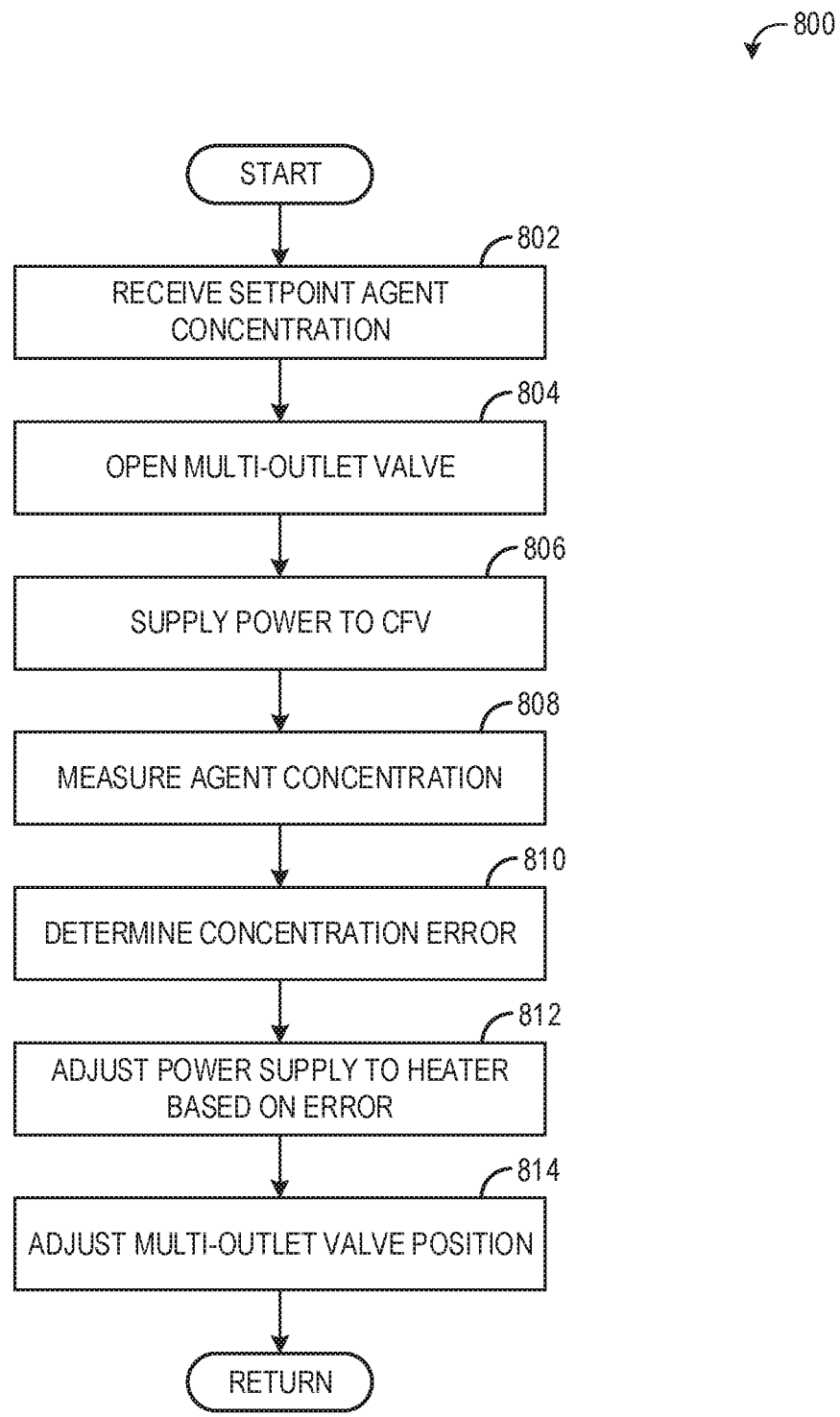
FIG. 8 is a flow chart illustrating a method for controlling the anesthetic agent delivery system of FIG. 1 or FIG. 2.

Turning now to FIG. 8, a method 800 for operating an anesthetic agent delivery system, such as the system 199 of FIG. 1, is shown. Method 800 may be carried out according to instructions stored in memory of a controller, such as controller 160 of FIG. 1, in conjunction with one or more sensors (e.g., sensors 120 and 140 of FIG. 1) and actuators (e.g., driver 148 and multi-outlet valve 108 of FIG. 1). Briefly, method 800 includes adjusting a power supply to the heating element of a CFV of the anesthetic agent delivery system in order to control the amount of anesthetic agent that is vaporized at a vapor reservoir and ultimately supplied to a patient. Method 800 also includes adjustment of a multi-outlet valve (also referred to as a proportional valve or splitting valve) to further control the amount of vaporized anesthetic agent provided to the patient, if desired or if the multi-outlet valve is present in the system. Method 800 may be executed to control additional or alternative systems, such as system 299 of FIG. 2.

At 802, method 800 includes receiving a setpoint agent concentration. The agent may be a suitable anesthetic agent, such as desflurane, isoflurane, sevoflurane, or the like, or another medication that may be inhaled/nebulized, such as albuterol. The setpoint agent concentration may include a percentage of the vaporized agent per volume of a fresh gas/agent mix provided to a patient. The setpoint agent concentration may be obtained via user input to the controller or other suitable mechanism.

At 804, method 800 includes opening the multi-outlet valve. The multi-outlet valve may be opened to a default open position, such as an open position where 20% of a fresh gas supply is supplied to the vapor reservoir (e.g., as carrier gas) and 80% of the fresh gas supply is bypassed around the vapor reservoir (e.g., as bypass gas). However, other open positions are possible, such a position based on a breathing rate/volume of the patient.

At 806, method 800 includes supplying power to the heater of the CFV. For example, the heater of the CFV may be a resistive heating element that increases in temperature as the current or voltage supplied to the heating element increases. The heater may be supplied with power in order to initiate vaporization of the liquid anesthetic agent that is drawn into the CFV, where the vaporized anesthetic agent is supplied to the vapor reservoir. A driver of the heating element may include a power supply (e.g., battery, capacitor, etc.) and power supply modulator (such as a buck-boost converter), and the controller may adjust the output voltage of the power supply modulator (e.g., by adjusting the duty cycle of a switching transistor of the converter) to adjust the supplied power to the heating element and ultimately the temperature of the heating element. The amount of power supplied to the heater of the CFV at 806 may be a default amount of power, such as an amount based on the setpoint agent concentration and boiling point of the anesthetic agent. In an example, the default valve position for the multi-outlet valve and the default heater temperature may be stored in look-up tables stored in memory of the controller, with anesthetic agent type, anesthetic agent setpoint concentration, and/or fresh gas flow rate as inputs to the look-up tables. Further, in examples where the agent vapor reservoir is charged with vapor prior to opening the multi-outlet valve, the look-up table for the multi-outlet valve may include a delay for opening the multi-outlet valve that is based on a desired vapor reservoir pressure, for example.

With the multi-outlet valve open and the heater of the CFV activated, anesthetic agent may begin to be supplied to the patient. As the agent and fresh gas mix is supplied to the patient, the mix flows past the agent concentration sensor (e.g., sensor 120 of FIG. 1). Thus, at 808, method 800 includes measuring the agent concentration. The agent concentration may be measured based on output from the agent concentration sensor. At 810, method 800 includes determining the agent concentration error. The concentration error may be the difference between the setpoint agent concentration and the measured agent concentration. At 812, method 800 includes adjusting the power supply to the heater based on the error. For example, if the error indicates the measured agent concentration is less than the setpoint concentration, the voltage or current supplied to the heating element may be increased to increase the temperature of the heater of the CFV and hence increase the amount of liquid anesthetic agent that is vaporized and supplied to the vapor reservoir. In one example, the power supply may be adjusted using a proportional-integral-derivative controller to drive the measured agent concentration toward the setpoint concentration.

At 814, method 800 optionally includes adjusting a position of the multi-outlet valve. In some systems, such as system 299 of FIG. 2, the vaporized anesthetic agent may be injected directly into the fresh gas flow, and thus no multi-outlet valve may be present in the system to adjust. However, in systems that include a multi-outlet valve for controlling the split between carrier gas and bypass gas, the proportion of carrier gas may be adjusted relative to the proportion of bypass gas in order to adjust the agent concentration supplied to the patient. In some examples, the position of the multi-outlet valve may be adjusted only once the heater adjustment is saturated (e.g., once the heating element is at a maximum temperature), as the adjustment to the heater may be faster and provide more accurate control over the agent concentration than adjustments to the multi-outlet valve. In other examples, the multi-outlet valve may be adjusted independently of the adjustment to the heater, for example based on a difference between a pressure in the vapor reservoir (e.g. as measured by sensor 140) and a pressure in the gas passage where the vaporized anesthetic agent mixes with fresh gas (e.g., at or upstream of junction 116). If the vapor reservoir pressure is higher than the gas passage pressure, adjusting of the position of the multi-outlet valve may not be needed, or the multi-outlet valve may be adjusted to flow less fresh gas through the vapor reservoir. If the vapor reservoir pressure is lower than the gas passage pressure, the position of the multi-outlet valve may be adjusted (e.g., to increase the flow of fresh gas through the vapor reservoir). Method 800 then returns, to continue to measure agent concentration and adjust the heater and/or multi-outlet valve based on the error between the setpoint and measured agent concentration, until the system is deactivated and anesthetic agent is no longer supplied to the patient.

Thus, method 800 of FIG. 8 provides for a closed-loop control routine where measured anesthetic agent concentration within an agent/fresh gas mix is used to control a temperature of a heating element of a capillary force vaporizer. In this way, the amount of anesthetic agent supplied to a patient may be precisely controlled with a relatively fast response time (e.g., relative to controlling the amount of anesthetic agent only by adjusting the amount of carrier gas that flows through the vapor reservoir). In some examples, the amount of vaporized anesthetic agent actually supplied to the patient may be further based on conditions of the vapor reservoir, such as the pressure in the vapor reservoir. For example, the pressure of the vapor reservoir may be maintained below a threshold pressure to ensure that the vaporized anesthetic agent in the vapor reservoir does not condense back into liquid anesthetic agent in the vapor reservoir and to maintain a safe pressure level within the vapor reservoir. Thus, if the pressure of the vapor reservoir (e.g., as measured by pressure sensor 140 of FIG. 1) increases to the threshold pressure, the multi-outlet valve position may be adjusted to lower the vapor pressure within the vapor reservoir and/or the temperature of the heating element of the CFV may be reduced to decrease the amount of vaporized anesthetic agent supplied to the vapor reservoir.

Figure 9:
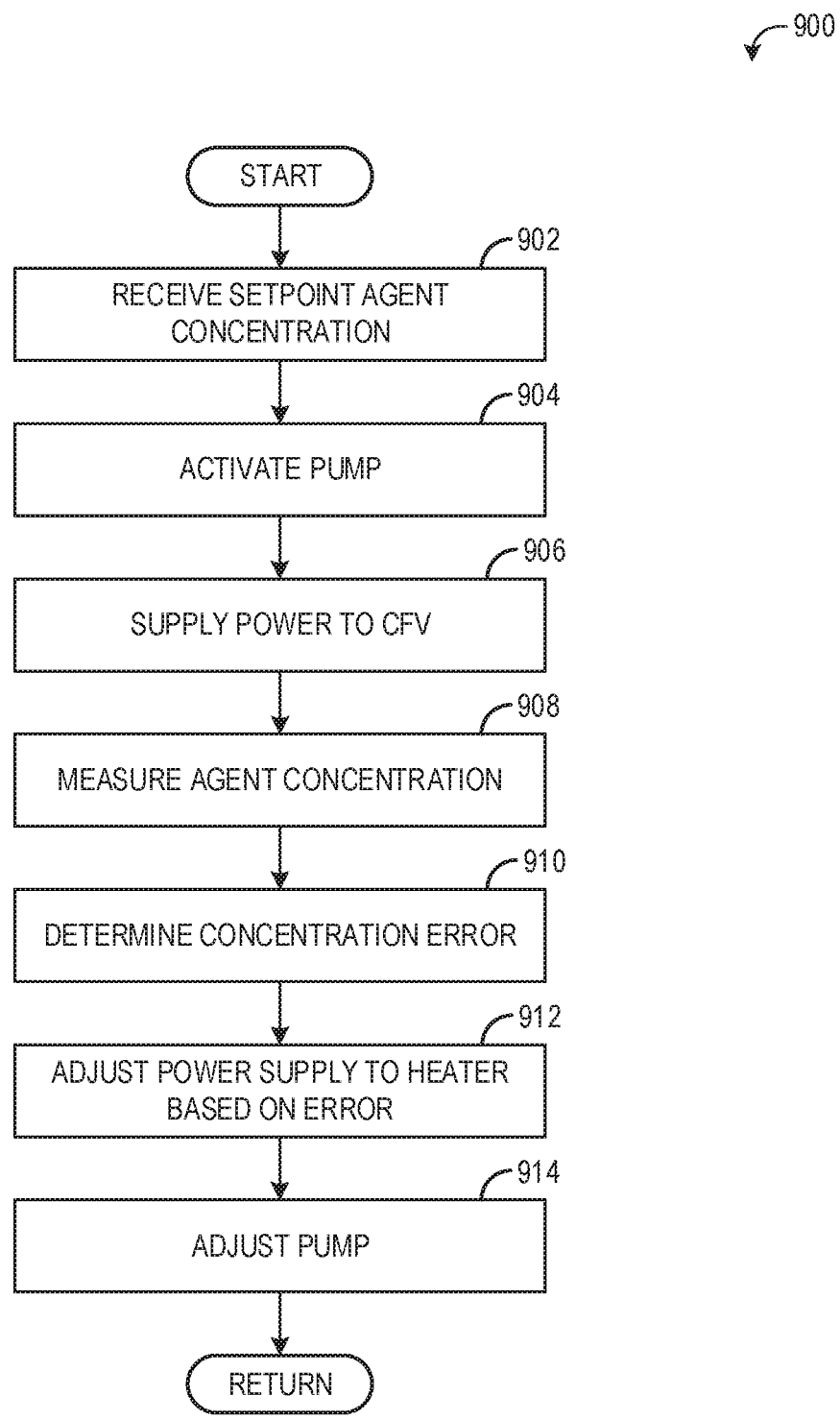
FIG. 9 is a flow chart illustrating a method for controlling the anesthetic agent delivery system of FIG. 3 or FIG. 3.

FIG. 9 shows a method 900 for operating an anesthetic agent delivery system, such as the system 399 of FIG. 3 and/or system 499 of FIG. 4. Method 900 may be carried out according to instructions stored in memory of a controller, such as controller 360 or 460, in conjunction with one or more sensors (e.g., sensors 320, 420) and actuators (e.g., driver 348 or 448). Briefly, method 900 includes adjusting a power supply to the heating element of a CFV of the anesthetic agent delivery system in order to control the amount of anesthetic agent that is vaporized at a vapor reservoir and ultimately supplied to a patient. Method 900 also includes adjustment of syringe pump or other suitable pump supplying liquid anesthetic agent to the CFV to ensure sufficient anesthetic agent is supplied to maintain commanded anesthetic agent concentration.

At 902, method 900 includes receiving a setpoint agent concentration. The agent may be a suitable anesthetic agent, such as desflurane, isoflurane, sevoflurane, halothane, or the like, or another medication that may be inhaled/nebulized, such as albuterol. The setpoint agent concentration may include a percentage of the vaporized agent per volume of a fresh gas/agent mix provided to a patient. The setpoint agent concentration may be obtained via user input to the controller or other suitable mechanism.

At 904, method 900 includes activating a pump, such as syringe pump 322 or 422. The pump may be coupled to a CFV and activation of the pump may result in liquid anesthetic agent being supplied to the CFV. At 906, method 900 includes supplying power to the heater of the CFV. For example, the heater of the CFV may be a resistive heating element that increases in temperature as the current or voltage supplied to the heating element increases. The heater may be supplied with power in order to initiate vaporization of the liquid anesthetic agent that is drawn into the CFV. A driver of the heating element may include a power supply (e.g., battery, capacitor, etc.) and power supply modulator (such as a buck-boost converter), and the controller may adjust the output voltage of the power supply modulator (e.g., by adjusting the duty cycle of a switching transistor of the converter) to adjust the supplied power to the heating element and ultimately the temperature of the heating element. The amount of power supplied to the heater of the CFV at 906 may be a default amount of power, such as an amount based on the setpoint agent concentration and boiling point of the anesthetic agent. In an example, the default pump position and the default heater temperature may be stored in look-up tables stored in memory of the controller, with anesthetic agent type, anesthetic agent setpoint concentration, and/or fresh gas flow rate as inputs to the look-up tables.

With the pump activated and the heater of the CFV activated, anesthetic agent may begin to be vaporized and released to a fresh gas flow and ultimately supplied to a patient. As the agent and fresh gas mix is supplied to the patient, the mix flows past an agent concentration sensor (e.g., sensor 320 of FIG. 3 or 420 of FIG. 4). Thus, at 908, method 900 includes measuring the agent concentration. The agent concentration may be measured based on output from the agent concentration sensor. At 910, method 900 includes determining the agent concentration error. The concentration error may be the difference between the setpoint agent concentration and the measured agent concentration.

At 912, method 900 includes adjusting the power supply to the heater based on the error. For example, if the error indicates the measured agent concentration is less than the setpoint concentration, the voltage or current supplied to the heating element may be increased to increase the temperature of the heater of the CFV and hence increase the amount of liquid anesthetic agent that is vaporized and supplied to the vapor reservoir. In one example, the power supply may be adjusted using a proportional-integral-derivative controller to drive the measured agent concentration toward the setpoint concentration.

At 914, method 900 includes adjusting the pump. For example, if the error indicates that additional anesthetic agent is to be supplied to meet the setpoint (e.g., the heating element temperature is increased), the amount of liquid anesthetic agent vaporized by the CFV may be increased. To ensure the CFV does not run dry or is otherwise unable to meet the setpoint concentration, the pump may be adjusted to adjust the amount of liquid anesthetic agent supplied to the CFV. The adjustment may include adjusting an actuator of the pump to move the pump plunger/seal to further pressurize the agent in the pump, forcing additional agent out of the pump and into the CFV. Method 900 then returns, to continue to measure agent concentration and adjust the heater and pump based on the error between the setpoint and measured agent concentration, until the system is deactivated and anesthetic agent is no longer supplied to the patient.

Figure 10:
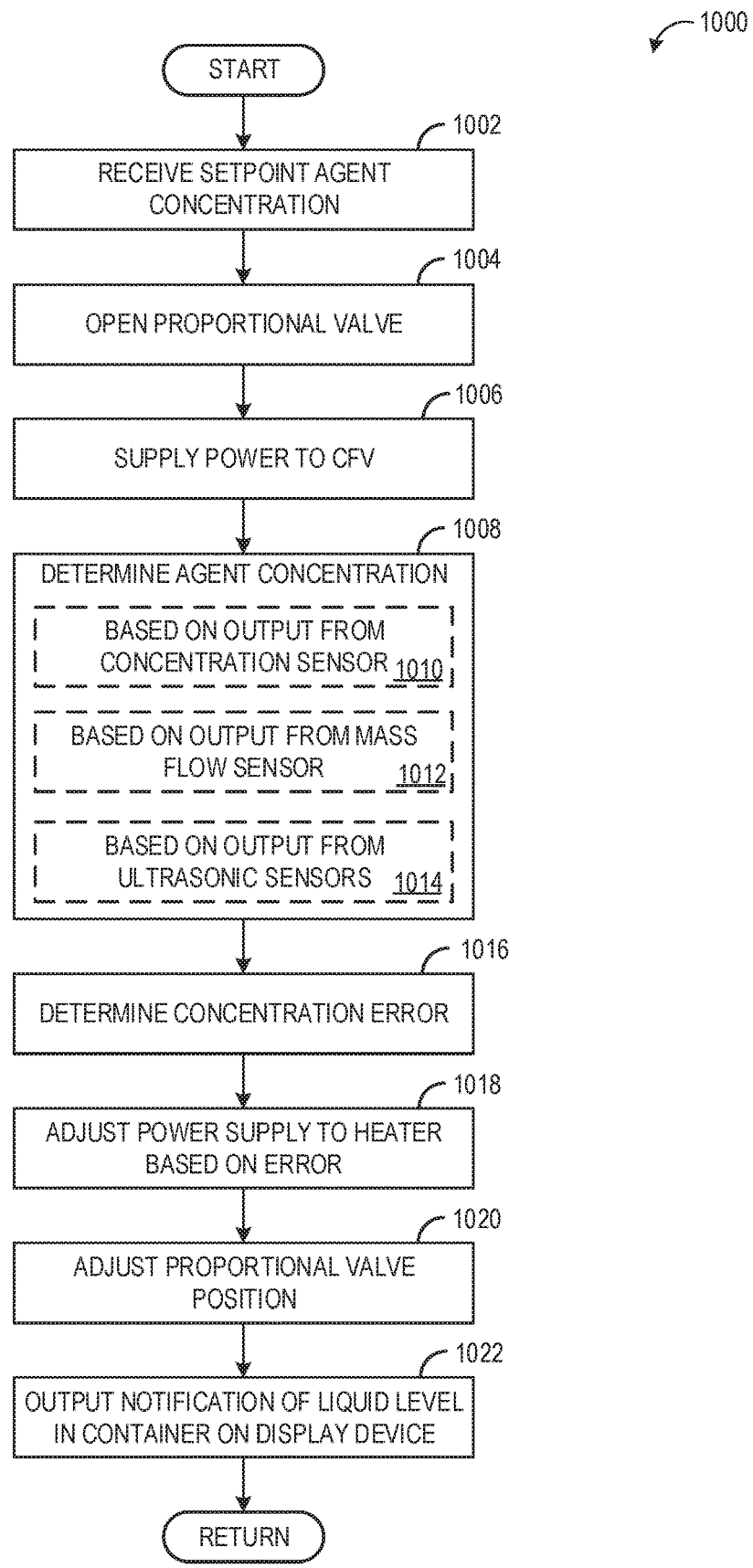
FIG. 10 is a flow chart illustrating a method for controlling the anesthetic agent delivery system of FIG. 5, FIG. 6, or FIG. 7.

FIG. 10 shows a method 1000 for operating an anesthetic agent delivery system, such as the system 599 of FIG. 5, system 699 of FIG. 6, or system 799 of FIG. 7. Method 1000 may be carried out according to instructions stored in memory of a controller, such as controller 588 of FIG. 5, controller 688 of FIG. 6, or controller 788 of FIG. 7, in conjunction with one or more sensors (e.g., sensors 520, 645, 715, and/or 717) and actuators (e.g., driver 575). Briefly, method 1000 includes adjusting a power supply to the heating element of a CFV of the anesthetic agent delivery system in order to control the amount of anesthetic agent that is vaporized at a vapor reservoir and ultimately supplied to a patient. Method 1000 may also include adjustment of a multi-outlet valve (also referred to as a proportional valve or splitting valve) to further control the amount of vaporized anesthetic agent provided to the patient, if desired or if the multi-outlet valve is present in the system.

At 1002, method 1000 includes receiving a setpoint agent concentration. The agent may be a suitable anesthetic agent, such as desflurane, isoflurane, halothane, sevoflurane, or the like, or another medication that may be inhaled/nebulized, such as albuterol. The setpoint agent concentration may include a percentage of the vaporized agent per volume of a fresh gas/agent mix provided to a patient. The setpoint agent concentration may be obtained via user input to the controller or other suitable mechanism.

At 1004, method 1000 includes opening a proportional valve, such as valve 524 of FIG. 5 or valve 724 of FIG. 7. The proportional valve may be positioned downstream of the vapor reservoir and may control the amount of vaporized anesthetic agent (as well as the amount of carrier gas) supplied to the patient. The proportional valve may be initially opened to a default position, such as fully open. In some examples, the proportional valve may be opened prior to activation of the CFV (described below). In other examples, the proportional valve may be maintained closed until after the CFV has been activated and the vapor reservoir has been charged with vaporized anesthetic agent (e.g., the proportional valve may be opened once the pressure in the vapor reservoir has reached a threshold pressure).

Some systems, such as system 699 of FIG. 6, include a multi-outlet valve upstream of the vapor reservoir rather than a proportional valve, in order to control the split between carrier gas and bypass. In such examples, the multi-outlet valve may be opened to a default open position, such as an open position where 20% of a fresh gas supply is supplied to the vapor reservoir (e.g., as carrier gas) and 80% of the fresh gas supply is bypassed around the vapor reservoir (e.g., as bypass gas). However, other open positions are possible, such a position based on a breathing rate/volume of the patient.

At 1006, method 1000 includes supplying power to the heater of the CFV. For example, the heater of the CFV may be a resistive heating element that increases in temperature as the current or voltage supplied to the heating element increases. The heater may be supplied with power in order to initiate vaporization of the liquid anesthetic agent that is drawn into the CFV, where the vaporized anesthetic agent is supplied to the vapor reservoir. A driver of the heating element may include a power supply (e.g., battery, capacitor, etc.) and power supply modulator (such as a buck-boost converter), and the controller may adjust the output voltage of the power supply modulator (e.g., by adjusting the duty cycle of a switching transistor of the converter) to adjust the supplied power to the heating element and ultimately the temperature of the heating element. The amount of power supplied to the heater of the CFV at 1006 may be a default amount of power, such as an amount based on the setpoint agent concentration and boiling point of the anesthetic agent. In an example, the default valve position for the proportional valve (and/or for the multi-outlet valve) and the default heater temperature may be stored in look-up tables stored in memory of the controller, with anesthetic agent type, anesthetic agent setpoint concentration, and/or fresh gas flow rate as inputs to the look-up tables. Further, in examples where the agent vapor reservoir is charged with vapor prior to opening the multi-outlet valve or proportional valve, the look-up table for the multi-outlet valve or proportional valve may include a delay for opening the multi-outlet valve or proportional valve that is based on a desired vapor reservoir pressure, for example.

With the proportional valve (or multi-outlet valve) open and the heater of the CFV activated, anesthetic agent may begin to be supplied to the patient. As the agent and fresh gas mix is supplied to the patient, the concentration of the vaporized anesthetic agent in the mix supplied to the patient may be determined at 1008, and the heater of the CFV may be controlled to reach the setpoint agent concentration. Depending on the configuration of the system, the agent concentration may be determined in different ways, as described below.

In one example, determining the agent concentration may include determining the agent concentration based on output from an agent concentration sensor (e.g., sensor 520 of FIG. 5), as indicated at 1010. In another example, determining the agent concentration may include determining the agent concentration based on output from a pair of mass flow sensors (e.g., sensor 645 and sensor 675 of FIG. 6), as indicated at 1012. For example, the first mass flow sensor (e.g., sensor 645) may measure the mass flow rate of the fresh gas supplied to the patient (where a portion of the fresh gas may be routed through the vapor reservoir, but ultimately all the fresh gas is supplied to the patient). The second mass flow sensor (e.g., sensor 675) may measure the mass flow rate of the combined, mixed gas (bypass gas and carrier gas) delivered to the patient. The difference in mass flow as measured by the two sensors may be used to determine the concentration of anesthetic agent being supplied to the patient, as the molar mass of the specific agent being delivered is known by the system. For example, a liquid anesthetic agent bottle (e.g., unit 661) may include an identification mechanism that transmits information regarding the anesthetic agent to the controller (e.g., RFID, EEPROM), where the information may include the molar mass of the anesthetic agent.

In other examples, to achieve additional simplification and cost reduction, mass flow sensor 675 may be omitted, and the amount of vaporized anesthetic agent may be estimated based on the pressure of the vapor reservoir (as measured by pressure sensor 650), temperature of the vapor reservoir (as measured by temperature sensor 654), temperature of the CFV (as determined based on the voltage or current supplied to the heating element of the CFV), and/or position of the multi-outlet valve (as determined by the commanded position of the multi-outlet valve). Thus, by measuring the mass flow of the fresh gas and estimating the amount of vaporized agent, the concentration of the vaporized agent in the fresh gas flow supplied to the patient may be determined.

In another example, determining the agent concentration may include determining the agent concentration based on output from one or more ultrasonic sensors (e.g., sensors 715 and 717 of FIG. 7), as indicated at 1014. For example, a first ultrasonic sensor (e.g., sensor 717) may measure a first speed of sound of fresh gas in a gas passage upstream of the vapor reservoir, where the fresh gas flows without any anesthetic agent. A second ultrasonic sensor (e.g., sensor 715) may measure a second speed of sound of fresh gas and vaporized anesthetic agent in the gas passage downstream of the vapor reservoir and proportional valve, where both fresh gas and vaporized anesthetic agent flows. The first speed of sound may be subtracted from the second speed of sound (or vice versa) to determine the contribution of the vaporized anesthetic agent to the second speed of sound, which may then be used to determine the concentration of the vaporized anesthetic agent in the fresh gas/agent mix (knowing the acoustic properties of the anesthetic agent, which may be determined empirically in advance and stored in memory of the controller, for example). Additionally or alternatively, the speed of sound information (e.g. time-of-flight) from the upstream sensor to the downstream sensor may be compared to the speed of sound (e.g., time-of-flight) from the downstream sensor to the upstream sensor. The difference in the speed of sound (e.g. time-of-flight) between the two measurements may be used to calculate the flow rate of the fresh gas, given the known cross sectional area of the gas passage and the distance between the ultrasonic transducers.

At 1016, method 1000 includes determining the agent concentration error. The concentration error may be the difference between the setpoint agent concentration and the determined agent concentration. At 1018, method 1000 includes adjusting the power supply to the heater based on the error. For example, if the error indicates the measured agent concentration is less than the setpoint concentration, the voltage or current supplied to the heating element may be increased to increase the temperature of the heater of the CFV and hence increase the amount of liquid anesthetic agent that is vaporized and supplied to the vapor reservoir. In one example, the power supply may be adjusted using a proportional-integral-derivative controller to drive the measured agent concentration toward the setpoint concentration.

At 1020, method 1000 optionally includes adjusting a position of proportional valve (or the multi-outlet valve). The proportional valve (or the multi-outlet valve) may be adjusted according to a user input (e.g., specifying an increase in fresh gas mass flow), based on power supplied to the heater, and/or based on pressure in the vapor reservoir relative to pressure in the gas passage (as explained above with respect to FIG. 5). In some examples, the position of the proportional valve (or multi-outlet valve) may be adjusted only once the heater adjustment is saturated (e.g., once the heating element is at a maximum temperature), as the adjustment to the heater may be faster and provide more accurate control over the agent concentration than adjustments to the proportional valve. In other examples, the proportional valve (or multi-outlet valve) may be adjusted independently of the adjustment to the heater, e.g., at the same time. The adjustment to the proportional valve may take into account the ambient pressure and temperature (as determined by sensors 546 and 548, 646 and 648, or 746 and 748). Additionally, the proportional valve may be controlled based on the output from the upstream ultrasonic sensor (e.g., sensor 717) or mass flow sensor 645. This same arrangement and capability is applicable to the ultrasonic sensor 715 or mass flow sensor 675, whereby the mixed gas (bypass gas and carrier gas) flow rate may be measured and compared to the inlet fresh gas flow rate. Dependent on the sensitivity of the flow measurements generated by the sensors, this may enable pneumatic leak detection within the vaporizer assembly if the flow measurements do not agree with each other within a pre-determined threshold. Likewise, given fresh gas flow rate information the upstream mass flow or ultrasonic sensor, the controller may adjust the heater and proportional valve accordingly, to respond rapidly to user input concentration and fresh gas flow setting changes. One non-limiting example may include implementation of a feed-forward control scheme, whereby a significant step increase in heating is commanded to the vaporizer and the proportional valve is commanded to open to its maximum (e.g., fully open position) to rapidly accommodate a user input step change from a lower fresh gas flow and concentration to a higher fresh gas flow.

At 1022, method 1000 may include outputting a notification of a liquid level of liquid anesthetic agent in the liquid anesthetic agent container (such as container 580) for display on a display device (e.g., a display operably coupled to the controller). The liquid level may be determined based on feedback from a liquid level sensor, such as sensor 594. For example, once the liquid level drops below a threshold, an operator of the system may remove an anesthetic agent container/CFV unit (of which the liquid anesthetic agent container may be a part), such as unit 561, and replace the unit with a fresh unit (which may be pre-filled with the appropriate liquid anesthetic agent).

Method 1000 then returns, to continue to measure agent concentration and adjust the heater and/or proportional/multi-outlet valve based on the error between the setpoint and determined agent concentration, until the system is deactivated and anesthetic agent is no longer supplied to the patient.

Thus, method 1000 of FIG. 10 provides for a closed-loop or open-loop control routine where a determined anesthetic agent concentration within an agent/fresh gas mix is used to control a temperature of a heating element of a capillary force vaporizer. In this way, the amount of anesthetic agent supplied to a patient may be precisely controlled with a relatively fast response time (e.g., relative to controlling the amount of anesthetic agent only by adjusting the amount of carrier gas that flows through the vapor reservoir). In some examples, the amount of vaporized anesthetic agent actually supplied to the patient may be further based on conditions of the vapor reservoir, such as the pressure in the vapor reservoir. For example, the pressure of the vapor reservoir may be maintained below a threshold pressure to ensure that the vaporized anesthetic agent in the vapor reservoir does not condense back into liquid anesthetic agent in the vapor reservoir. Thus, if the pressure of the vapor reservoir increases to the threshold pressure, the multi-outlet valve or proportional valve position may be adjusted to lower the pressure in the vapor reservoir (e.g., such that less carrier gas enters the reservoir), the outflow valve (e.g., valve 726) may be closed, and the pressurized vapor within the vapor reservoir may directed to the scavenge passage (e.g., passage 728) and the scavenging valve (e.g., valve 730) to decrease pressure within the vapor reservoir (e.g., reservoir 734) to a suitable value. In addition to the closure of the outflow valve and redirection of the agent vapor to scavenging, the temperature of the heating element of the CFV may be reduced to decrease the amount of vaporized anesthetic agent supplied to the vapor reservoir.

A technical effect of a capillary force vaporization anesthetic agent delivery system is precise control of delivered anesthetic agent that can be adjusted in a closed-loop feedback manner. Another technical effect of the capillary force vaporization anesthetic agent delivery system is the ability to package the capillary force vaporizer in a combined unit with a pre-filled anesthetic agent container, reducing operator exposure to the anesthetic agent and the risk for contamination.

In another representation, a system for delivering an anesthetic agent includes an anesthetic agent reservoir, a capillary force vaporizer (CFV) fluidically coupled to the anesthetic agent reservoir, and a vapor reservoir fluidically coupled to the CFV, the vapor reservoir fluidically coupled to a gas passage configured to flow fresh gas. In a first example, the CFV comprises a porous wick and a heating element. In a second example, which optionally includes the first example, the wick is comprised of alumina ceramic and the heating element comprises nichrome wire, strips, or ribbons coated in silicon nitride. In a third example, which optionally includes the first and/or second example, the system further includes an agent concentration sensor positioned in the gas passage. In a fourth example, which optionally includes one or more or each of the first through third examples, the system further includes a controller storing instructions executable to determine a concentration of the vaporized anesthetic agent in the gas passage, and adjust a temperature of the CFV based on a difference between the concentration of the vaporized anesthetic agent and a commanded concentration. In a fifth example, which optionally includes one or more or each of the first through fourth examples, the anesthetic agent reservoir comprises a syringe pump and the instructions are further executable to adjust an actuator of the syringe pump based on the difference. In a sixth example, which optionally includes one or more or each of the first through fifth examples, the CFV is housed within the anesthetic agent reservoir. In a seventh example, which optionally includes one or more or each of the first through sixth examples, the vapor reservoir is coupled to an inflow gas passage configured to supply fresh gas to the vapor reservoir. In an eighth example, which optionally includes one or more or each of the first through seventh examples, the vapor reservoir is coupled to an injector configured to inject vaporized anesthetic agent into a flow of fresh gas.

In another representation, a system includes a gas passage, a vapor reservoir having a gas inlet and gas outlet, an inflow passage coupling the gas passage at a first junction to the gas inlet of the vapor reservoir, an outflow passage coupling the gas outlet of the vapor reservoir to the gas passage at a second junction, a multi-outlet valve positioned at the first junction, an agent concentration sensor positioned in the gas passage downstream of the second junction, a capillary force vaporizer (CFV) coupled to a vapor inlet of the vapor reservoir, a liquid anesthetic agent reservoir coupled to the CFV, and a controller. The controller stores instructions executable to determine a concentration of the vaporized anesthetic agent in the gas passage downstream of the second junction, and adjust a temperature of the CFV based on a difference between the concentration of the vaporized anesthetic agent and a commanded concentration. In a first example, the instructions are further executable to adjust a position of the multi-outlet valve. In a second example, which optionally includes the first example, the gas passage is coupled to a gas source at a first end of the gas passage, the gas source configured to supply fresh gas to the gas passage. In a third example, which optionally includes the first and/or second examples, the commanded concentration is determined via a user input. In a fourth example, which optionally includes one or more or each of the first through third examples, the instructions are executable to adjust a temperature of the CFV by adjusting an amount of voltage or current supplied to a heating element of the CFV. In a fifth example, which optionally includes one or more or each of the first through fourth examples, the system includes a concentration sensor positioned in the gas passage and the instructions are executable to determine the concentration of vaporized anesthetic agent in the gas passage based on output from the concentration sensor.

In another representation, a system includes a gas passage, a vapor reservoir coupled to the gas passage via an injector, a capillary force vaporizer (CFV) coupled to a vapor inlet of the vapor reservoir, a liquid anesthetic agent reservoir coupled to the CFV, and a controller. The controller stores instructions executable to determine a concentration of the vaporized anesthetic agent in the gas passage downstream of the injector, and adjust a temperature of the CFV based on a difference between the concentration of the vaporized anesthetic agent and a commanded concentration. In a first example, the gas passage is coupled to a gas source at a first end of the gas passage, the gas source configured to supply fresh gas to the gas passage. In a second example, which optionally includes the first example, the commanded concentration is determined via a user input. In a third example, which optionally includes the first and/or second examples, the instructions are executable to adjust a temperature of the CFV by adjusting an amount of voltage or current supplied to a heating element of the CFV. In a fourth example, which optionally includes one or more or each of the first through third examples, the system includes a concentration sensor positioned in the gas passage and the instructions are executable to determine the concentration of vaporized anesthetic agent in the gas passage based on output from the concentration sensor.

In another representation, a system includes a gas passage including a mixing region, a capillary force vaporizer (CFV) housed within the mixing region, a syringe pump configured to dispense liquid anesthetic agent to the CFV, and a controller. The controller stores instructions executable to determine a concentration of vaporized anesthetic agent in the mixing region (or in the gas passage downstream of the mixing region), and adjust a temperature of the CFV based on a difference between the concentration of the vaporized anesthetic agent and a commanded concentration. In a first example, the gas passage is coupled to a gas source at a first end of the gas passage, the gas source configured to supply fresh gas to the gas passage. In a second example, which optionally includes the first example, the commanded concentration is determined via a user input. In a third example, which optionally includes the first and/or second examples, the instructions are executable to adjust a temperature of the CFV by adjusting an amount of voltage or current supplied to a heating element of the CFV. In a fourth example, which optionally includes one or more or each of the first through third examples, the instructions are further executable to adjust an actuator of the syringe pump based on the difference. In a fifth example, which optionally includes one or more or each of the first through fourth examples, the syringe pump is coupled to the CFV via a supply passage. In a sixth example, which optionally includes one or more or each of the first through fifth examples, the syringe pump is directly coupled to the CFV at a wall of the mixing region.

In another representation, a method for delivering anesthetic agent to a patient includes activating a capillary force vaporizer (CFV) to supply a flow of vaporized anesthetic agent to a gas passage; determining a concentration of the vaporized anesthetic agent in the gas passage; and adjusting a temperature of a heating element of the CFV based on the measured concentration. In a first example, the method further includes receiving a user input of a setpoint anesthetic agent concentration. In a second example, which optionally includes the first example, adjusting a temperature of a heating element of the CFV based on the measured concentration includes determining a difference between the measured concentration and the setpoint concentration, and adjusting the temperature of the heating element based on the difference.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A liquid anesthetic agent container, comprising:
   a base region, an interior of the base region holding liquid anesthetic agent;
   an adapter region; and
   a capillary force vaporizer (CFV) housed in the adapter region, the adapter region including a coupling end configured to couple to a vapor reservoir of a patient breathing circuit to supply vaporized anesthetic agent vaporized by the CFV to a patient, the CFV including a heating element, a temperature of the heating element controllable by a driver of the patient breathing circuit based on a concentration of the vaporized anesthetic agent estimated from at least a pressure of the vapor reservoir as measured by a pressure sensor coupled to the vapor reservoir.

2. The liquid anesthetic agent container of claim 1, wherein the coupling end includes a fastener configured to couple to a complementary fastener of the patient breathing circuit.

3. The liquid anesthetic agent container of claim 2, wherein the patient breathing circuit includes an anesthesia machine including the vapor reservoir, wherein the complementary fastener comprises a port of the anesthesia machine, and wherein when the adapter region is coupled to the vapor reservoir via the port, the anesthetic agent vaporized by the CFV is configured to flow to a gas passage of the anesthesia machine.

4. The liquid anesthetic agent container of claim 3, wherein the adapter region includes an electrical connection configured to electrically couple the heating element of the CFV to the driver, and wherein the concentration of the vaporized anesthetic agent is estimated from the pressure of the vapor reservoir and further based on a mass flow of fresh gas in the gas passage and one or more of a temperature of the vapor reservoir, a temperature of the CFV, and a position of a multi-outlet valve positioned upstream of the vapor reservoir.

5. The liquid anesthetic agent container of claim 4, wherein the CFV comprises a wick, the wick extending into an interior of the liquid anesthetic agent container.

6. The liquid anesthetic agent container of claim 5, wherein the driver is positioned at a bottom of the vapor reservoir.

7. The liquid anesthetic agent container of claim 1, wherein the adapter region forms a neck of the liquid anesthetic agent container.

8. A system, comprising:
   a liquid anesthetic agent container including a base region configured to hold liquid anesthetic agent, an adapter region, and a capillary force vaporizer (CFV) housed in the adapter region, the adapter region including a coupling end and a first electrical connector; and
   a patient gas machine including a port configured to couple to the coupling end of the liquid anesthetic agent container and a second electrical connector configured to couple to the first electrical connector, the port of the patient gas machine coupled to a vapor reservoir and where vaporized anesthetic agent is configured to flow to the patient gas machine via the port, the patient gas machine further including a controller and a proportional valve positioned downstream of the vapor reservoir and configured to control an amount of the vaporized anesthetic agent supplied to a patient, the controller storing instructions executable to adjust an amount of power supplied to a heating element of the CFV via the first electrical connector and the second electrical connector and adjust a position of the proportional valve based on the amount of power supplied to the heating element.

9. The system of claim 8, wherein the patient gas machine comprises an anesthesia machine.

10. The system of claim 8, wherein the patient gas machine comprises a ventilator.

11. The system of claim 8, wherein the patient gas machine includes a gas passage configured to flow fresh gas and adapted to fluidically couple to an outlet of the CFV, the patient gas machine further including at least one sensor coupled to the gas passage.

12. The system of claim 11, wherein the controller stores instructions executable to adjust the amount of power supplied to the heating element to adjust a temperature of the heating element based on output from the at least one sensor.

13. The system of claim 12, wherein the at least one sensor comprises a mass flow sensor, and wherein the instructions are executable to adjust the temperature of the heating element responsive to an estimated concentration of vaporized anesthetic agent differing from a setpoint concentration, the estimated concentration of vaporized anesthetic agent determined at least in part from output of the mass flow sensor.

14. The system of claim 12, wherein the at least one sensor comprises a concentration sensor, and wherein the instructions are executable to adjust the temperature of the heating element responsive to a measured concentration of vaporized anesthetic agent differing from a setpoint concentration.

15. A system, comprising:
a liquid anesthetic agent container including a base region and an interior configured to hold liquid anesthetic agent;
a capillary force vaporizer (CFV) housed in an adapter configured to couple to the base region, the CFV including a heating element;
a vapor reservoir coupled to the adapter;
a gas passage configured to flow fresh gas, the gas passage fluidically coupled to the vapor reservoir at a first junction;
a proportional valve positioned in an outflow passage coupled to the vapor reservoir and the gas passage at a second junction, downstream of the first junction;
at least one sensor coupled to the gas passage downstream of the second junction; and
a controller storing non-transitory instructions executable to:
determine a concentration of vaporized anesthetic agent in the gas passage downstream of the vapor reservoir based on output from the at least one sensor;
adjust a temperature of the heating element based on a difference between the determined concentration and a setpoint concentration; and
adjust a position of the proportional valve based on the temperature of the heating element and/or a pressure of the vapor reservoir.

16. The system of claim 15, wherein the at least one sensor comprises a concentration sensor positioned in the gas passage downstream of the vapor reservoir, and wherein adjusting the position of the proportional valve based on user input, the temperature of the heating element, and/or the pressure of the vapor reservoir comprises adjusting the position of the proportional valve based on the pressure of the vapor reservoir to maintain the pressure of the vapor reservoir below a maximum pressure above which condensation of the vaporized anesthetic agent occurs.

17. The system of claim 15, wherein the at least one sensor comprises a first ultrasonic sensor positioned in the gas passage upstream of the vapor reservoir and a second ultrasonic sensor positioned in the gas passage downstream of the vapor reservoir.

18. The system of claim 17, wherein the instructions are executable to determine the concentration of the vaporized anesthetic agent by:
determining a first speed of sound in the gas passage upstream of the vapor reservoir based on output from the first ultrasonic sensor;
determining a second speed of sound in the gas passage downstream of the vapor reservoir based on output from the second ultrasonic sensor; and
determining the concentration of the vaporized anesthetic agent based on a difference between the first speed of sound and the second speed of sound.

19. The system of claim 12, wherein adjusting the position of the proportional valve comprises adjusting the position of the proportional valve in response to the temperature of the heating element reaching a maximum temperature.

20. The system of claim 12, wherein the instructions are further executable to initiate the supply of power to the heating element to activate the heating element while the proportional valve is closed and open the proportional valve once a threshold pressure of the vapor reservoir is reached.

* * * * *